United States Patent
Miki et al.

(10) Patent No.: US 6,706,010 B1
(45) Date of Patent: Mar. 16, 2004

(54) BALLOON CATHETER AND METHOD OF PRODUCTION THEREOF

(75) Inventors: Shogo Miki, Suita (JP); Kohei Fukaya, Settsu (JP); Takuji Nishide, Settsu (JP); Masato Hashiba, Settsu (JP); Ryoji Nakano, Settsu (JP); Hiromi Maeda, Uji (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/529,081

(22) PCT Filed: Oct. 7, 1998

(86) PCT No.: PCT/JP98/04539
§ 371 (c)(1),
(2), (4) Date: Apr. 7, 2000

(87) PCT Pub. No.: WO99/17831
PCT Pub. Date: Apr. 15, 1999

(30) Foreign Application Priority Data

| Oct. 8, 1997 | (JP) | H09-275685 |
| Oct. 31, 1997 | (JP) | H09-316064 |
| Feb. 5, 1998 | (JP) | H10-024941 |
| Mar. 12, 1998 | (JP) | H10-060828 |

(51) Int. Cl.[7] ............ A61M 3/00; A61M 29/00; A61M 25/00

(52) U.S. Cl. ............ 604/43; 604/264; 604/103; 604/96.01

(58) Field of Search ............ 264/512; 604/96.01, 604/102.02, 167.03, 103.1, 523, 103, 913, 103.05, 103.04, 103.09, 160, 43; 209/447; 128/898; 152/370; 606/194, 192

(56) References Cited

U.S. PATENT DOCUMENTS

| 4,317,692 A | * | 3/1982 | Niconchuk ............ 152/370 |
| 4,335,723 A | * | 6/1982 | Patel ............ 604/103 |
| 5,370,616 A | * | 12/1994 | Keith et al. ............ 604/102.02 |
| 5,423,754 A | * | 6/1995 | Cornelius et al. ............ 604/103 |
| 5,549,552 A | * | 8/1996 | Peters et al. ............ 604/103.1 |
| 5,587,125 A | * | 12/1996 | Roychowdhury ............ 264/512 |
| 5,634,092 A | * | 5/1997 | Stokes ............ 345/418 |
| 5,634,902 A | * | 6/1997 | Johnson et al. ............ 604/96.01 |
| 5,707,357 A | * | 1/1998 | Mikhail et al. ............ 604/167.03 |
| 5,810,867 A | * | 9/1998 | Zarbatany et al. ............ 604/96.01 |
| 5,846,220 A | * | 12/1998 | Elsberry ............ 128/898 |
| 5,891,110 A | * | 4/1999 | Larson et al. ............ 604/523 |
| 5,921,957 A | * | 7/1999 | Killion et al. ............ 604/96.01 |
| 6,066,157 A | * | 5/2000 | Barbere ............ 604/96.01 |
| 6,342,120 B1 | * | 1/2002 | Basta ............ 156/242 |

FOREIGN PATENT DOCUMENTS

| JP | 1-145074 | 6/1989 |
| JP | 4-2363 | 1/1992 |
| JP | 6-114108 | 4/1994 |
| JP | 8-215312 | 8/1996 |

* cited by examiner

*Primary Examiner*—Michael J. Hayes
*Assistant Examiner*—Roz Ghafoorian
(74) *Attorney, Agent, or Firm*—Armstrong, Westerman & Hattori, LLP

(57) ABSTRACT

It is an object of the present invention to provide a balloon catheter in which the inner tube is prevented from slackening after balloon inflation, improving the rewrapping of the balloon, discontinuity in the rigidity of the joined portions of the outer tube and the balloon is lessened, which prevents breakage, and the catheter advances through blood vessels better and passes more easily through narrow segments, preventing the catheter from "accordioning" and enhancing insertion force transmission. The balloon catheter pertaining to the present invention has a catheter shaft (1) with a double-tube structure comprising an outer tube (4) and an inner tube (5), and a balloon (3) disposed at the distal end portion of this catheter shaft (1). A guide tube (11) having an outside diameter smaller than the inside diameter of the outer tube (4) and having an inside diameter larger than the outside diameter of the inner tube (5) is disposed at least at the distal end portion of the outer tube (4) so as to form a double-tube with the outer tube (4), and the inner tube (5) is not fixed, but passes through the interior of the guide tube (11) in the axial direction.

32 Claims, 16 Drawing Sheets

BALLOON CATHETER AND METHOD OF PRODUCTION THEREOF

TECHNICAL FIELD

This invention relates to a balloon catheter used in percutaneous transluminal angioplasty (PTA) or percutaneous transluminal coronary angioplasty (PTCA), in which constricted areas or obstructions such as in the coronary artery, limb arteries, the renal artery, or peripheral vessels are treated by dilation, and to a method for manufacturing this balloon catheter, and more particularly relates to a balloon catheter with improved characteristics for the catheter shaft distal end portion, including the balloon, and to a method for manufacturing this balloon catheter.

BACKGROUND ART

A balloon catheter is generally made up of a catheter shaft and a vascular dilation balloon provided to the distal end portion of this catheter shaft. Angioplasty using a balloon catheter such as this is conducted by the following procedure. First, a guide wire is passed through the afflicted site (such as an obstruction), the balloon catheter is inserted along this guide wire until the balloon is at the afflicted site, and the balloon is inflated by supplying a suitably diluted contrast medium or the like to an inflation lumen. After this inflation, the balloon is depressurized and deflated, and the balloon catheter is taken out of the body.

A specific example of a conventional balloon catheter, and the problems encountered with it, will now be described.

FIG. 5 illustrates the cross sectional structure of a conventional balloon catheter at its distal end portion. In the figure, 80 is a catheter shaft, 81 is an inner tube, 82 is an outer tube, 83 is a balloon, and 84 is an X-ray impermeable marker. The proximal end 85 of the balloon 83 provided at the distal end portion of the catheter shaft 80 is joined to the distal end portion of the outer tube 82, and the distal end 86 of the balloon 83 is joined in the proximity of the distal end portion of the inner tube 81. When this balloon 83 is depressurized and deflated, it wraps up as shown in FIG. 6. The following problems were encountered when a balloon catheter with a structure such as this was used at an afflicted site with a high degree of difficulty. When the surgeon applied force to the proximal end of the balloon catheter so as to align the balloon at a highly constricted site, the thin-walled balloon 83 deformed like a bellows (called "accordioning"), so the force applied to the proximal end was not sufficiently transmitted to the distal end, making it much more difficult for the catheter to pass through the afflicted site, and the balloon could not be accurately aligned with the constricted area. The cause of this was that the outer tube 82 and inner tube 81 were fixed to branched hubs, or the like, at the proximal end of the catheter, and were therefore securely restrained, and were weakly linked via just the thin-walled balloon 83 at the distal end portion, so the middle part between the distal end and proximal end portions was not restrained at all.

Balloon catheters with the structure illustrated in FIG. 7 have been proposed in an effort to solve this problem (see, for example, Japanese Laid-Open Patent Applications H3-51059, H4-2363, and H5-137793). In the figure, 90 is a catheter shaft, 91 is an inner tube, 92 is an outer tube, 93 is a balloon, and 94 is an X-ray impermeable marker. Specifically, since the inner tube 91 was joined to the inner wall surface of the outer tube 92 in the proximity of the distal end portion of the outer tube 92, and the outer tube 92 and the inner tube 91 were securely restrained by this joint 95, the balloon 93 did not accordion even at difficult afflicted sites with severe constriction, and the pushing force applied by the surgeon was transmitted to the distal end portion. Nevertheless, the following problems were encountered with these balloon catheters.

In the positioning and inflation of the balloon at the afflicted site, the balloon extends radially and longitudinally due to the pressure applied by a pressurizing fluid, but the inner tube inside the balloon, that is, the inner tube located between the distal end portion proximity of the outer tube and the distal end portion proximity of the balloon, is stretched along with the longitudinal extension of the balloon. Then, when the dilation of the afflicted site is completed and the balloon is deflated, the balloon 93 returns to its original dimensions because it is made from a pressure-resistant type of material, but as shown in FIG. 8, the stretched inner tube 91 does not return to its original length, and instead slackens. The reason for this is that because the inner tube is usually made from a material selected for its ability to slide smoothly over the guide wire, it does not exhibit the elastic changes that the balloon does, and is instead prone to plastic deformation and is easily stretched. In this state, the position of the inner tube is shifted with respect to the folding creases in the balloon, and this makes it much more difficult to rewrap the balloon when it is deflated, resulting in winging, and if another attempt is made to pass the catheter through the constriction, the wings often snag and prevent the catheter from passing through. Specifically, once the balloon has been inflated, it passes through the afflicted site with more difficulty the second and subsequent times. This situation is illustrated in FIGS. 9 and 10. FIG. 9(*a*) shows the state when the wings of the balloon 93 are wrapped in opposite directions around the inner tube 91, and FIG. 9(*b*) shows the state in which the wings 93*a* and 93*b* are not wrapped sufficiently and stick out. FIG. 10(*a*) shows the state when the wings of the balloon 93 are wrapped in the same direction around the inner tube 91, and FIG. 10(*b*) shows the state in which the wings 93*a* and 93*b* are not wrapped sufficiently and stick out.

A problem that is common to both of the balloon catheters shown in FIGS. 5 and 7 is that since the rigidity varies greatly in the outer tube distal end portion, this portion is prone to breakage when the balloon catheter is handled or when the guide wire is replaced. This is because the only things beyond the outer tube distal end portion are the slender inner tube and the thin-walled balloon, so discontinuity in the rigidity occurs.

Problems related to the very farthest point at the distal end portion of a conventional balloon catheter will now be described through reference to FIGS. 21 to 26. FIG. 21 is an enlarged cross section illustrating the very farthest point at the distal end portion of a balloon catheter. In the figure, 100 is a balloon and 101 is an inner tube. The inner tube 101 goes through and sticks out from the distal end portion of the balloon 100, and is bonded to the distal end-side bonded portion of this balloon by an adhesive agent layer 103. The distal end portion of the inner tube 101 retains the tubular shape of the inner tube, and has an edge 104 at the most distal end portion. A problem with this edge 104, however, was that it would snag when passing through the afflicted site in a blood vessel or through a curved section, making it difficult to pass the catheter through these areas.

In view of this, prior art has been proposed in which just the edge portion of the most distal end of the inner tube is removed, but at afflicted sites with a high degree of constriction, for instance, the difficulty of passing through the afflicted site or through curved sections has not been solved to satisfaction. Prior art in which the distal end tip of the balloon catheter is made flexible in order to improve this passage has been proposed in Japanese Laid-Open Patent Applications H2-271873 and H5-253304. Both of these disclose a structure in which the sleeve portion 111 (121) of the distal end portion of a balloon 110 (120) sticks out from an inner tube 112 (122) that forms a guide wire lumen (see FIGS. 22 and 23, which are simplified cross sections of the distal end tip). Here, in the example shown in FIG. 22, the outside diameter of the sleeve portion 111 formed integrally with the balloon 110 is reduced in steps toward the distal end, and in the example shown in FIG. 23, the outside diameter of the sleeve portion 121 is reduced to a pointed taper shape toward the distal end. In recent years, however, it has become necessary for a balloon to have better pressure-resistance strength, which has created the need to fabricate the balloon from a relatively hard material that stretches less. As a result, the distal end tip formed in this sleeve portion needs to have high rigidity.

Furthermore, the distal end tip needs to be slender in order to facilitate its passage. Prior art to this end includes the balloon catheter with a constricted most distal end portion at the distal end tip disclosed in International Laid-Open Patent Application WO88/6465, in which the sleeve of the balloon distal end portion is fused to the tube (inner tube) that forms the guide wire lumen, forming two layers of tube and sleeve, after which these two layers are chamfered.

The above-mentioned Japanese Laid-Open Patent Application H2-271873 discloses a structure in which the sleeve portion of the distal end portion of the balloon sticks out from the inner tube distal end portion, and the sleeve portion of the balloon forms the most distal end portion of the catheter. The effect of this is stated to be that the distal end tip is more flexible because the fixed surface area is increased and the fixing distance between the inner tube and the sleeve of the balloon distal end portion is shortened, and that the balloon distal end portion can be prevented from peeling away at the fixed portion between the inner tube and the sleeve of the balloon distal end portion during catheter insertion because this fixed portion is not exposed on the outer surface of the catheter. More recently, however, it has become necessary for the distal end tip to be both flexible and smaller in diameter, and while it was possible to achieve flexibility by increasing the fixed surface area and reducing the fixing distance between the inner tube and the sleeve of the balloon distal end portion, constricting or tapering the two-layer portion comprising the tube and sleeve was difficult due to the structure, and there seemed to be an insurmountable limit to how much the two-layer portion could be reduced in diameter. Also, there was an abrupt step where the two layers changed to a single layer, and this posed a serious obstacle to curving the balloon catheter distal end portion and passing it through afflicted sites with a high degree of constriction.

Also, the medical profession is now demanding catheters that will pass easily through afflicted sites with a high degree of difficulty, afflicted sites with a high degree of curvature, and portions with high surface resistance, such as through a stent.

To meet this demand, a catheter will have to be even slimmer and more flexible. Specifically, a balloon catheter needs to be slender enough that it can just squeeze through the gap through which the guide wire passes, and to be able to closely follow the guide wire as it enters acutely curved afflicted sites (see FIGS. 24 and 25). In FIGS. 24 and 25, 130 is a balloon, 131 is a sleeve on the far side of the balloon 130, 132 is a distal end tip, 132a is the distal end portion of the distal end tip, 133 is a guide wire, 140 is a blood vessel, 140a is a constriction, and 140b is a branched blood vessel branching off from the blood vessel 140. If the catheter is not able to follow the guide wire adequately into afflicted sites with a large degree of curvature or branched afflicted sites with sharp angles, then the guide wire may break while the balloon catheter is advancing. Also, a stent 141 has often been used in recent years to maintain the diameter of a blood vessel dilated with a balloon catheter (see FIG. 26). In the event of reconstriction within this stent, or reconstriction near the distal end portions where the stent is left, a balloon catheter has to be moved into the stent once again, but the distal end tip 132 may run into the coiled portion (strut) of the stent 141 and be unable to proceed any further, among other problems that are encountered.

Problems related to the joining of a conventional catheter shaft and balloon will now be described through reference to FIGS. 27 and 28. Means such as heat fusion and adhesive bonding have been used in the past to join a catheter shaft and a balloon, and various methods have been provided. For instance, Japanese Laid-Open Patent Application S61-92677 (Medical Tube with Attached Balloon) discloses a technique related to adhesive bonding, in which a tube and a balloon made of different materials are bonded with an adhesive agent composed of an addition polymerization type of silicone composition. All that is discussed here is that different materials can be bonded, and no mention is made about the properties of the adhesive agent, and particularly its hardness, after it cures. If the hardness of the adhesive agent portion is far higher than that of the catheter shaft or balloon, the rigidity will be discontinuous for the catheter as a whole, and when the balloon catheter is passed through a curved section within a blood vessel, it will be difficult for the balloon catheter to conform to the curved blood vessel, as shown schematically in FIGS. 27 and 28. In FIGS. 27 and 28, 150 is a catheter shaft to which a balloon 151 has been bonded with an adhesive agent of high hardness, 152 is a guide wire, 153a is a curved section of a coronary artery, for example, and 153b is a constriction.

In this case, the surgeon does not merely feel resistance as the balloon catheter is moved forward, and this is actually extremely dangerous, as there is the possibility that kinks 154a and 154b in the catheter could injure the blood vessel at the portion of discontinuous rigidity. Also, if the adhesive agent is very hard after curing, then the distal end tip will also be hard, making it extremely difficult to insert the catheter into the constriction 153b.

Meanwhile, when heat fusion is used, it is not effective for all combinations of catheter shaft and balloon materials, and is therefore limited to combinations with which the miscibility of the resins is good when they are heat-fused. Therefore, this method is generally employed when the catheter shaft and balloon are made of the same material, and does not lend itself well to the joining of a catheter shaft and balloon made of different materials. Even when a catheter shaft and balloon made of different materials with good miscibility are heat-fused, the fused portion often becomes harder than the catheter shaft, which results in discontinuity in the rigidity of the catheter shaft and, at the same time, inevitably leads to a loss of flexibility in the distal end tip.

A conventional balloon, and the problems encountered with conventional balloons, will now be described. In general, a balloon must be strong enough not to burst when pressure is applied to the balloon, and must be such that the inflation can be safely controlled to the desired size, among other requirements. Also, the properties must be such that if the balloon should burst inside a blood vessel, it will be a tearing burst in the axial direction, which poses relatively little danger, rather than a pinhole burst that could damage the blood vessel or a tearing burst in the radial direction, which makes the balloon more difficult to remove from the blood vessel after bursting. It is also desirable for the walls of the balloon to be as thin as possible and for the balloon to have a small coefficient of friction so that it can pass through extremely constricted sections with ease. Also, it is important for the balloon to be made of a material with which no wings will be produced when the balloon is rewrapped as discussed above. Other requirements include the ability of the balloon to conform to and easily bend in curved sections of a blood vessel.

Materials that have been used in or proposed for conventional balloons include polyethylene terephthalate, polyethylene, polyvinyl acetate, ionomers, polyvinyl chloride, polyamide, polyamide-based thermoplastic elastomers, polyester-based thermoplastic elastomers, and polyurethane-based thermoplastic elastomers.

Because of its strength, a polyethylene terephthalate (PET) material can be molded into a thin-film pressure-resistant balloon, and is a typical material having low expansion characteristics, as disclosed in Japanese Laid-Open Patent Application S63-26655 and Japanese Patent Publication H3-37941. A balloon composed of PET, however, lacks flexibility at room temperature and near body temperature because its glass transition point is over 60° C., and thus inflation takes a long time, and when the balloon is inflated at a high pressure, there is a serious danger of injuring the afflicted site. This material is also difficult to wrap and is prone to the above-mentioned winging, so it tends to scratch blood vessels. Furthermore, because the glass transition point is so high, and the balloon is in an excessively crystalline state at room temperature or near body temperature, the balloon is susceptible to wrinkling, and pinhole bursting tends to occur at these wrinkles.

A balloon formed from polyethylene, polyvinyl acetate, an ionomer, polyvinyl chloride, or a copolymer or mixture of these has relatively low material strength, so only low pressure resistance can be obtained. Thus, to achieve the required inflation pressure resistance, the walls of the balloon have to be made thicker. Wrapping is facilitated by making the walls thicker, but the drawback is that the wrapped balloon has a larger diameter and is bulkier.

A balloon formed from a polyamide material has high pressure resistance comparable to that of a PET material, and also has some flexibility, so the problems encountered with PET, namely, winging during wrapping and susceptibility to pinhole bursting, are ameliorated to a certain extent. Because of the high tensile strength of a polyamide material, however, the walls of the balloon are made thinner, and consequently shape retention is poor in the wrapping of the balloon, and winging tends to occur during rewrapping. Also, a polyamide material has a relatively large coefficient of friction and is highly hygroscopic, so inside a blood vessel, which is a particularly humid environment, a problem is the large amount of friction with the vascular walls. Methods for manufacturing a balloon using a polyamide material are discussed in Japanese Laid-Open Patent Applications H3-57462 and H3-57463. These manufacturing methods entail numerous steps, including a heat fixing step, in addition to the process being complicated and difficult to control, so drawing unevenness tends to occur in the balloon, and circumferential tear bursting may occur during the use of the balloon, so there is the danger of damaging the blood vessels.

A balloon composed of a polyurethane, polyamide-based thermoplastic elastomer, polyester-based thermoplastic elastomer, or other such block copolymer is excellent because it is sufficiently strong and is flexible, but because it is softer than a polyamide, its shape retention in wrapping is poor. Therefore, a heat treatment must be performed to impart shape retention, but this heat treatment is difficult, the balloon diameter shrinks severely when exposed to an elevated temperature during sterilization, and it is extremely difficult to control the final balloon diameter. Also, polyamide-based thermoplastic elastomers are often used to modify polyamide resins, and polyester-based thermoplastic elastomer are used to modify polyester resins, but polyamide-based thermoplastic elastomers and polyester-based thermoplastic elastomers generally have a high modulus elasticity and are not readily modified in terms of increasing flexibility, and their miscibility with other resins is also poor. Thus, a drawback to these materials is that they can only be used in applications limited to the above-mentioned combinations.

Various balloon materials were described above, but none of these balloon materials could satisfy the expansion characteristics required of a balloon. This is because the desired expansion characteristics of a balloon for an afflicted site are not constant. Specifically, a balloon must be inflated under a relatively high pressure for afflicted sites such as those where severe calcification has occurred, so the balloon must be able to withstand this inflation pressure, and it is preferable for the balloon to have low expandability, wherein changes in balloon diameter are relatively small with respect to changes in inflation pressure. On the other hand, in the case of a large afflicted site, it is preferable for the balloon to have high expandability, so that its size when inflated can match the size of the afflicted site.

Because of the difficulty of fabricating a balloon having the characteristics of both low and high expandability using a single type of material, the balloon must be made from a combination of two or more types of material, but this is extremely disadvantageous for industrial purposes because of the higher costs involved, etc. To fabricate a balloon with high expandability, a material with relatively low strength must be selected, and as a result, the walls of the balloon inevitably have to be made thicker to achieve pressure resistance, and because this makes the balloon diameter larger when wrapped, the balloon catheter does not pass through narrow sections well. From the standpoint of enhancing shape retention when the balloon is wrapped, it is advantageous for the balloon walls to be thinner, but then the strength is inadequate. Meanwhile, if a high-strength material is used and the balloon walls are made thin, the balloon will have little flexibility during wrapping, and it will not adequately fulfill its function as a balloon catheter. There has been a need for a balloon material that would have a good balance between these two conflicting characteristics.

In light of the above problems, the following (1) to (4) are objects of the present invention.

(1) To provide a balloon catheter that solves all of the problems regarding ease of use encountered in the past. Specifically, to provide a balloon catheter that solves these problems by preventing the inner tube from slackening after balloon inflation and thereby improving the rewrapping of the balloon, preventing breakage through a reduction in the discontinuity of the rigidity of the joined portions of the outer tube and the balloon, adjusting the hardness of the shaft of the balloon portion so as to improve passage through afflicted sites with severe constriction and through curved blood vessels, and preventing "accordioning" so as to enhance the transmission of the pushing force.

(2) To make the distal end tip of the balloon catheter more flexible and slender, and markedly improve conformability to the guide wire and passage through constrictions.

(3) To provide a balloon catheter that not only has sufficient strength after the catheter shaft and balloon have been joined and integrated as compared to a conventional method for joining a catheter shaft and balloon, but also has no discontinuity in the catheter shaft rigidity related to the hardness of the bonded portion, is able to conform easily to curved blood vessels, and has a distal end tip that remains flexible after the curing of the adhesive agent.

(4) To provide a balloon catheter equipped with a balloon that has excellent flexibility and pressure resistance, is easily wrapped, retains its shape when wrapped, and is easily rewrapped after being inflated.

DISCLOSURE OF THE INVENTION

To achieve the stated objects, the balloon catheter of the present invention is a balloon catheter having a catheter shaft with a double-tube structure comprising an outer tube and an inner tube through which a guide wire is passed, located at least in the proximity of the distal end portion of the catheter, a inflation lumen through which a pressure fluid is passed being provided between the inner tube and the outer tube, and a balloon disposed at the distal end portion of the catheter shaft and capable of being inflated, deflated, and wrapped by the pressure fluid, wherein the end of the balloon on the proximal side is joined in the proximity of the distal end portion of the inner tube, and a guide tube having an outside diameter smaller than the inside diameter of the outer tube and having an inside diameter larger than the outside diameter of the inner tube is disposed so as to form a double-tube with the outer tube, and the inner tube is not fixed, but passes through the interior of the guide tube in the axial direction.

With this structure, even though the inner tube is stretched when the balloon is inflated, the inner tube is able to slide through the guide tube in the axial direction, so the stretching is within the range of elastic deformation, and the inner tube returns to its original state when the balloon is deflated. Also, the rigidity of the joined portions of the outer tube and balloon is continuous, preventing any breakage in these portions.

It is preferable here for the guide tube to be joined in a state of being offset to the inner wall surface of the outer tube. This makes it possible for the walls to be thinner in the joined portion of the guide tube with respect to the outer tube, and ensures a good flow of the balloon inflation pressurized fluid that flows through the inflation lumen between the outer tube and inner tube.

By having the distal end of the guide tube butted up against the proximal end side of an X-ray impermeable marker joined to the inner tube, or having the distal end of the guide tube butted up against the joint of the balloon where it is joined to the inner tube, the pushing force applied from the proximal side of the outer tube of the catheter shaft will be more readily transmitted to the distal end portion of the inner tube via the guide tube.

By making the guide tube walls thinner toward the distal end, the hardness of the shaft of the balloon portion can be adjusted so that it continuously becomes softer nearer to the distal end.

When the distal end of the guide tube is butted up against the joint between the inner tube and the balloon distal end, an X-ray impermeable marker is provided over the outer surface of the guide tube.

It is preferable for the guide tube to be composed of a polyimide, or to be composed of one or more members of the group consisting of polyamide elastomers, polyester elastomers, polyurethane elastomers, and polyolefin elastomers.

Here, if a spring-like coil is embedded in the guide tube, this coil will increase the rigidity of the guide tube with respect to the transmitted pushing force, and the hardness can be suitably adjusted with respect to curvature. In this case, the spring-like coil is preferably composed of an X-ray impermeable material.

It is also preferable if the inner tube protrudes from the balloon distal end portion, and a distal end tip formed at the junction with the distal end portion has a pointed taper shape, and the wall thickness of the distal end taper portion decreases continuously in the distal end tip from the proximity of the most distal end of the distal end-side balloon joint up to the most distal end of the catheter, the average thickness reduction gradient is 6 to 60 $\mu$m/mm, the length from the most distal end of the distal end-side balloon joint to the most distal end of the catheter is 3 to 10 mm, and the tube wall thickness at the most distal end of the distal end taper portion is 10 to 50 $\mu$m.

It is even more favorable here if the average thickness reduction gradient of the distal end taper portion is 10 to 30 $\mu$m/mm, the length from the most distal end of the distal end-side balloon joint to the most distal end of the catheter is 4 to 7 mm, and the tube wall thickness at the most distal end of the distal end taper portion is 20 to 40 $\mu$m.

If the average thickness reduction gradient of the distal end taper portion exceeds 60 $\mu$m/mm, the distal end portion from the distal end to the proximal side will suddenly become hard, making it difficult for the distal end tip to conform to the guide wire. On the other hand, if this average thickness reduction gradient is less than 6 $\mu$m/mm, the wall thickness of the taper portion most distal end portion will increase and hinder catheter passage, or the distal end tip will be too long and the frictional resistance will be great as the catheter passes through the afflicted site. It is therefore preferable for the average thickness reduction gradient to be adjusted to 6 to 60 $\mu$m/mm. A setting of 10 to 30 $\mu$m/mm is even better.

As to the length of the distal end tip from the most distal end of the distal end-side balloon joint to the catheter most distal end, if the length of the distal end tip is less than 3 mm, then even if the average thickness reduction gradient is between 6 and 60 $\mu$m/mm, sufficient flexibility and a reduction in diameter at the distal end portion will not be achieved. On the other hand, if the length of the distal end exceeds 10 mm, a large force will be required to overcome the frictional resistance produced by the distal end tip and to pass through the afflicted site, the walls will be too thin in the distal end portion, and the distal end portion will be susceptible to being broken by the pushing force of the surgeon.

Furthermore, even if the average thickness reduction gradient is 6 to 60 $\mu$m/mm and the length of the distal end tip is between 3 and 10 mm, it is undesirable for the tube walls of the distal end taper portion most distal end to be either too thin or too thick, and it is preferable for the wall thickness of the most distal end to be set within a range of 10 to 50 $\mu$m while the above conditions are also met. If the tube wall thickness of the distal end tip most distal end is less than 10 $\mu$m, the distal end portion will be too soft and will stick to the guide wire, so the frictional resistance will be greater during pushing, resulting in the undesirable occurrence of "accordion" deformation. If the wall thickness is over 50 μm, though, the distal end tip will not be sufficiently flexible and no reduction in the diameter of the distal end portion will be obtained.

It is even more favorable to form an adhesive agent layer at the stepped portion produced between the inner tube and the most distal end of the distal end-side balloon joint so as to eliminate this step, decreasing the discontinuity in rigidity and the step in the proximity of the balloon catheter distal end portion. The step and the discontinuity in rigidity may also be decreased by forming the most distal end of the sleeve portion of the distal end-side balloon joint in a taper so as to eliminate the step.

Furthermore, it is preferable for the most distal end of the distal end taper portion to be chamfered, and for the inner tube to be composed of HDPE (High-Density PolyEthylene) or a fluororesin such as polytetrafluoroethylene.

The method for manufacturing a balloon catheter equipped with the above-mentioned distal end tip includes a step in which the portion of the inner tube forming the distal end taper portion is locally heated, a tensile force is applied to both ends of the portion to stretch it to a specific length, thereby constricting the inner tube, and this constricted portion is cut to a specific length, and the inner tube having the distal end taper portion is inserted into an outer tube, and the inner tube and the balloon distal end portion are joined so that the distal end taper portion protrudes from the balloon distal end portion, thereby forming the distal end tip.

The second method for manufacturing a balloon catheter equipped with the above-mentioned distal end tip includes a step in which the sleeve portion of a distal end-side balloon joint is joined to the inner tube, after which the most distal end of the sleeve portion is locally heated, a tensile force is applied to the balloon distal end portion and the heated inner tube on the distal end side to stretch it to a specific length, thereby constricting the inner tube and the most distal end in the sleeve portion, and this constricted portion is cut to a specific length, and the inner tube having the distal end taper portion is inserted into an outer tube, and the inner tube and the balloon distal end portion are joined so that the distal end taper portion protrudes from the balloon distal end portion, thereby forming the distal end tip.

The above-mentioned diameter reduction in the distal end tip and making it more flexible may be accomplished by working the inner tube that forms the guide wire lumen ahead of time and then assembling the balloon and other parts, or the distal end portion of an assembled balloon catheter may be worked. Reducing the diameter by working while the parts are not yet assembled is preferable from the standpoint of boosting assembly efficiency.

The distal end tip can be easily worked by locally heating part of the inner tube forming the guide wire lumen, and stretching to a specific length. In this case, it is preferable to form the distal end taper portion in a state in which a mandrel has been inserted into the inner tube that forms the guide wire lumen. As a different working method, an excimer laser may be used to achieve the desired wall thickness reduction gradient. Working takes longer with this method, but the wall thickness can be adjusted more accurately.

The easiest working method is abrasion with a file. This method, however, produces filings of the material, which is not suited to working in a clean room, and requires a washing step after the working.

As to the adhesive agent used to join the proximal end of the balloon in the proximity of the distal end portion of the outer tube and to join the distal end of the balloon in the proximity of the distal end portion of the inner tube, the durometer hardness (D value) when the adhesive agent is cured is preferably at least D16 and no more than D70.

Here, the adhesive agent is preferably either a two-liquid normal temperature (room temperature) curing type of adhesive agent, a UV-curing adhesive agent, or a water-absorption curing type of adhesive agent. It is even more favorable for the two-liquid normal temperature (room temperature) curing type of adhesive agent to be a urethane type, silicone type, or epoxy type, and also more favorable for the water-absorption curing type of adhesive agent to be a cyanoacrylate type of urethane type.

It is particularly preferable for the balloon pertaining to the present invention to be composed of a polymer alloy material including a styrene-based thermoplastic elastomer as a constituent component. It is preferable for the polymer alloy material to include one or more members of the group consisting of polyester resins, polyester-based thermoplastic elastomers, polyamide resins, polyamide-based thermoplastic elastomers, polyurethanes, and polyphenylene ethers as constituent components.

It is even better for the polymer alloy material to include a polyolefin as a constituent component.

It is favorable if the styrene-based thermoplastic elastomer is contained in an amount of 1 to 30 wt %, and if this styrene-based thermoplastic elastomer is a type that imparts functional groups. It is also favorable for the styrene-based thermoplastic elastomer to be a hydrogenation type.

If a styrene-based thermoplastic elastomer with good resin modification properties and excellent miscibility is thus used as one of the constituent components of the polymer blend in the balloon material pertaining to the present invention, the properties of the balloon thus formed, and particularly its flexibility, wrapability, wrapped shape retention, assembly workability, and so on, will be improved, and a wide range of control over expandability will be achieved, making it possible to provide a balloon that is thin-walled and pressure-resistant while having particularly high expandability. With this balloon material, materials that were immiscible in the past are miscibilized, and it is possible to combine a plurality of resins having favorable properties for a balloon, and as a result, a superior balloon in which the weak points of existing materials are compensated can be provided.

BEST MODE FOR CARRYING OUT THE INVENTION

Figure 1:
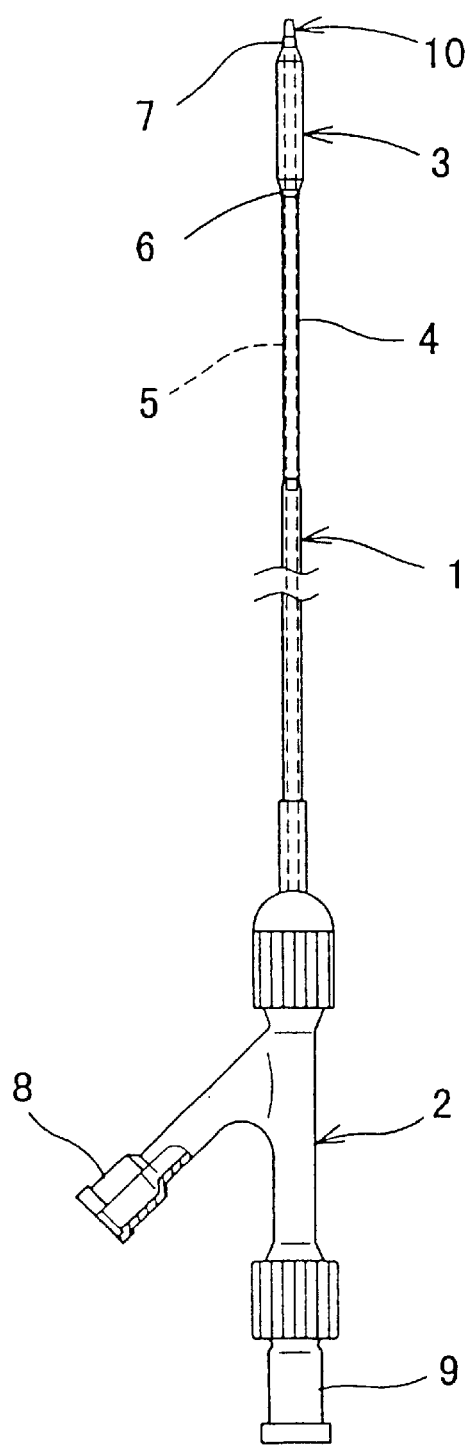
FIG. 1 is an overall side view illustrating an example of the balloon catheter pertaining to the present invention.

FIG. 1 is an overall side view illustrating a typical example of the over-the-wire balloon catheter pertaining to the present invention. The balloon catheter in this example has a structure in which a branched hub 2 is connected to the proximal end portion of a catheter shaft 1, and a balloon 3 is provided to the distal end portion of the catheter shaft 1. At least the distal end portion of the catheter shaft 1 has a double-tube structure in which an inner tube 5 is disposed inside an outer tube 4, and an inflation lumen (not shown) is provided in the space between the outer tube 4 and the inner tube 5 as a passageway for a pressure fluid that inflates, deflates, and wraps the balloon 3 through the application of pressure. This inflation lumen communicates with a pressure fluid inlet 8 provided to the branched hub 2. The inner tube 5 communicates with a guide wire inlet 9 provided to the branched hub 2 in the proximal end portion, and goes through the balloon 3 and opens in the distal end portion, and the distal end of the inner tube 5 extends to the far side beyond the distal end portion of the balloon 3. The inner peripheral surface of a sleeve 6 on the proximal end side of the balloon 3 is joined coaxially with the outer peripheral surface of the distal end portion of the outer tube 4, and a sleeve 7 on the distal end side of the balloon 3 is joined coaxially with the outer peripheral surface of the inner tube 5. The portion 10 on the far side beyond the proximity of the distal side sleeve 7 of the balloon 3 is called the distal end tip.

The present invention is characterized by the structure, shape, and material of the catheter distal end portion, including the balloon, and the balloon catheter of the present invention can therefore be applied not only as an over-the-wire type of balloon catheter, but also as a monorail type provided with a guide wire insertion hole midway along the catheter shaft.

Figure 2:
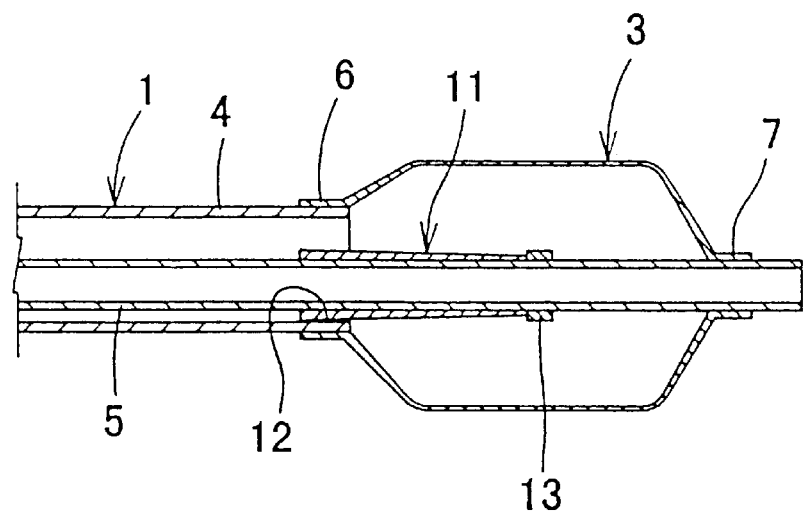
FIG. 2 is an enlarged cross section of the main components in one embodiment of the present invention.

FIG. 2 is an enlarged cross section of the distal end portion of the balloon catheter pertaining to the present invention. In the distal end portion of the outer tube 4 of the catheter shaft 1, a guide tube 11 whose outside diameter is smaller than the inside diameter of the outer tube 4 and whose inside diameter is larger than the outside diameter of the inner tube 5, is provided so as to form a double-tube with the outer tube 4, and the proximal end portion of the guide tube 11 is fixed at a joint 12 in a state of being offset in one direction to the inner wall surface of the outer tube 4. The distal end portion of the guide tube 11 extends into the balloon 3, and the inner tube 5 goes through the inside of the guide tube 11 without being fixed, and able to slide in the axial direction. Also, because the guide tube 11 has a tapered shape in which its walls become thinner toward the distal end, the hardness of the shaft in the balloon portion is adjusted to afford continuous flexibility toward the distal end.

Because the guide tube 11 and the inner tube 5 are in a slidable state as above, when the balloon 3 inflates and increases in length in the axial direction, the inner tube 5 joined to the sleeve 7 on the distal side of the balloon 3 slides through the guide tube 11, resulting in extremely little stretching of the inner tube 5 inside the balloon 3. When the balloon 3 is then deflated, the inner tube 5 again slides inside the guide tube 11, so there is no slackening or bending of the inner tube 5 whatsoever. Thus, rewrapping of the balloon 3 poses no problem, and there is no serious impediment to passage through afflicted sites after the second and subsequent wrappings. The presence of the guide tube also affords continuous rigidity in the joined portions of the outer tube 4 and the sleeve 6 on the proximal side of the balloon 3, thereby preventing breakage in these portions.

Here, because the guide tube 11 is joined to the outer tube 4 at the joint 12 in a state of being offset to the inner wall surface of the outer tube 4, the inner tube 5 can be supported such that it is offset with respect to the outer tube 4 in the distal end portion of the catheter shaft 1. Accordingly, the cross section of the inflation lumen between the outer tube 4 and the inner tube 5 is crescent-shaped, rather than the conventional ring shape, and this makes it easier for the pressure fluid to flow through the inflation lumen. Thus, the outside diameter of the distal end portion of the outer tube 4 can be partially reduced without impeding the flow of the pressure fluid, and the catheter shaft distal end portion can be kept from increasing in outside diameter by joining the proximal-side sleeve 6 at the place where this outside diameter has been reduced.

The distal end of the guide tube 11 is butted up against the proximal end of an X-ray impermeable marker 13 joined to the inner tube 5 located inside the balloon 3, and the pushing force applied from the proximal side of the outer tube 4 of the catheter shaft 1 is transmitted to the distal end portion of the inner tube 5 via the guide tube 11 joined to the distal end portion of the outer tube 4, and therefore the above-mentioned accordion deformation can be prevented.

From the standpoint of reducing the outside diameter when the balloon 3 is wrapped, a polyimide is the preferred material for the guide tube 11, and it is particularly favorable for the wall thickness thereof to be reduced to about 10 to 20 μm. From the standpoint of enhancing flexibility, it is preferable for the guide tube 11 to be made of at least one or more materials selected from among polyamide elastomers, polyester elastomers, polyurethane elastomers, and polyolefin elastomers.

Figure 3:
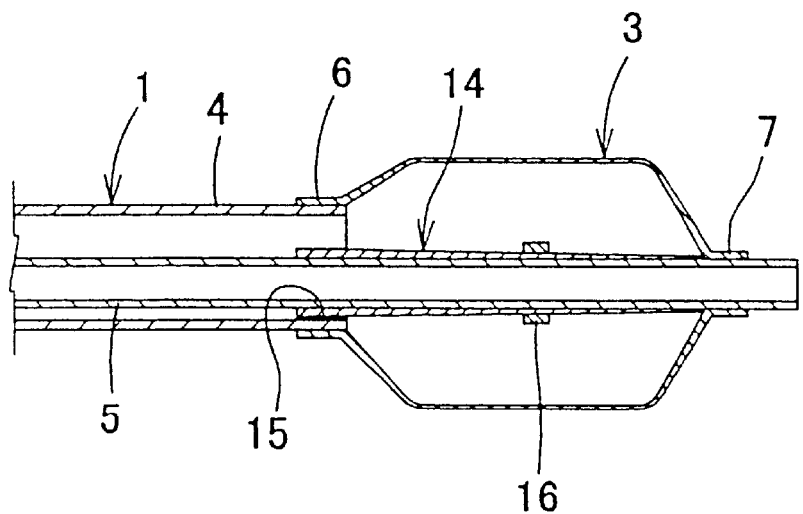
FIG. 3 is an enlarged cross section of the main components in another embodiment of the present invention.

Another embodiment of the present invention will now be described through reference to FIG. 3. The balloon catheter in this example is equipped with a guide tube 14 having the same pointed taper shape as above, but the proximal end portion of the guide tube 14 is joined at a joint 15 in a state of being offset to the inner wall surface in the distal end portion of the outer tube 4, and the distal end portion of the guide tube is inside the balloon 3 and butted up against the joint between the outer peripheral wall of the inner tube 5 and the sleeve 7 on the distal side of the balloon 3. With this structure, the pushing force applied from the proximal side of the outer tube 4 of the catheter shaft 1 is directly transmitted to the distal end portion of the inner tube 5 and the distal end portion of the balloon 3 via the guide tube 14, which prevents accordion deformation even more effectively. In addition, in this example an X-ray impermeable marker 16 is provided over the outer peripheral surface of the guide tube 14. The rest of the structure is the same as in the example given above, and the same structural components are labeled with the same numbers, and will not be described again.

Figure 4:
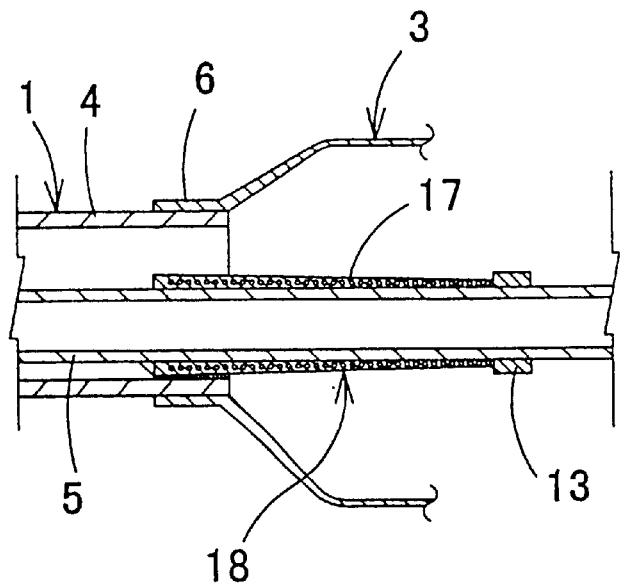
FIG. 4 is an enlarged cross section of the main components in yet another embodiment of the present invention.
Figure 5:
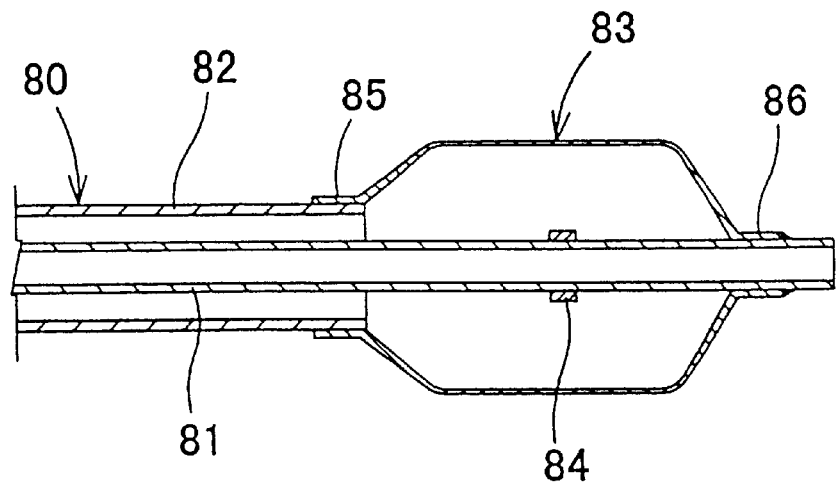
FIG. 5 is a partial cross section illustrating the structure of a typical conventional balloon catheter.
Figure 6:
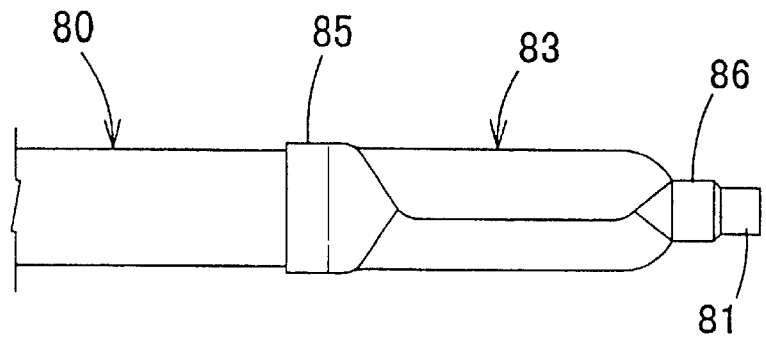
FIG. 6 is a partial side view of when the balloon has been wrapped.
Figure 7:
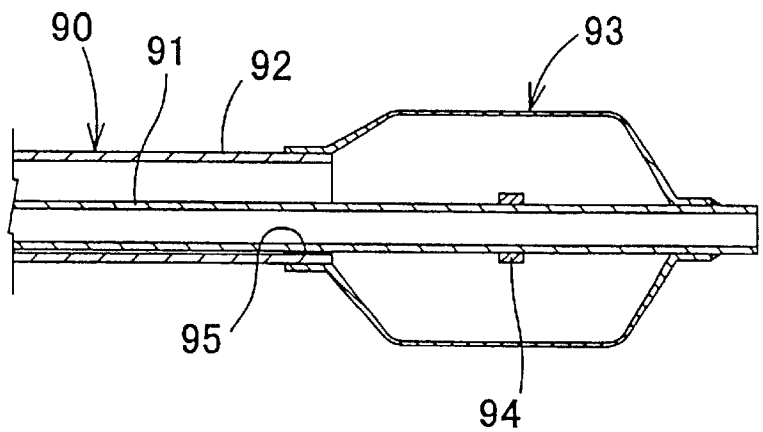
FIG. 7 is a partial cross section illustrating the structure of a conventional modified balloon catheter.
Figure 8:
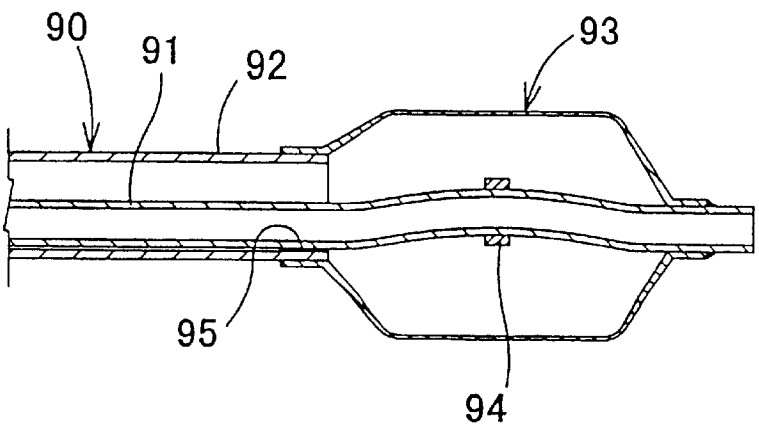
FIG. 8 is a partial cross section corresponding to FIG. 7 showing the illustrated balloon in the state after the balloon has been inflated and then deflated.
Figure 9:
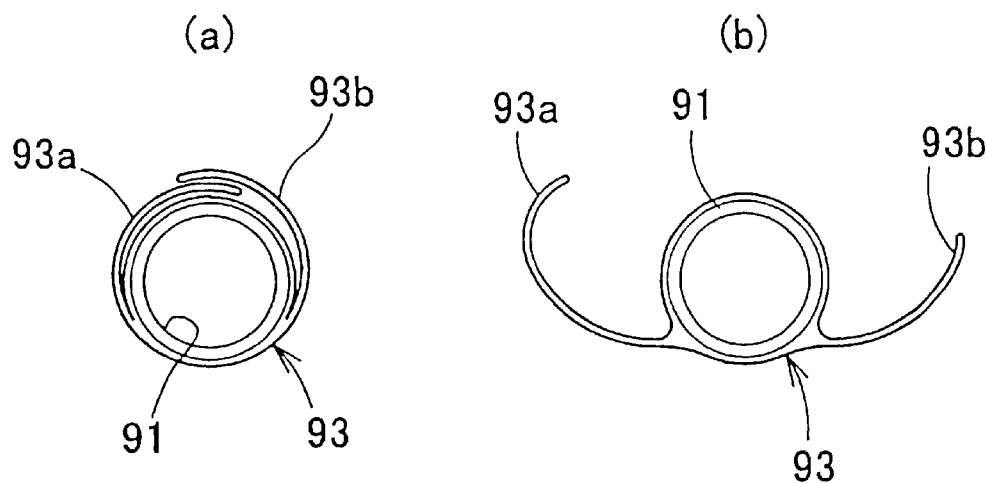
FIG. 9 is a cross section of a balloon wrapped with its wings wound in opposite directions, with (a) illustrating the normal wrapping and (b) improper wrapping in which winging has occurred.
Figure 10:
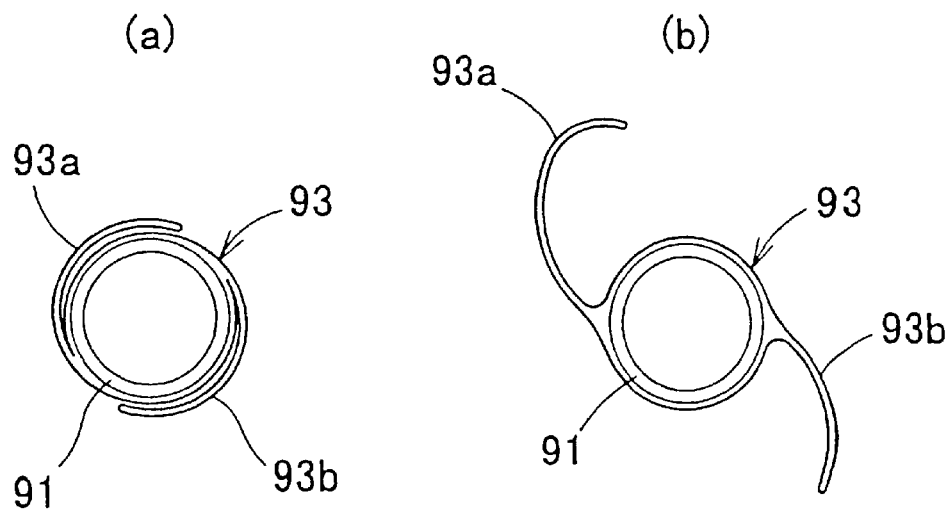
FIG. 10 is a cross section of a balloon wrapped with its wings wound in the same direction, with (a) illustrating the normal wrapping and (b) improper wrapping in which winging has occurred.

Yet another embodiment of the present invention will now be described through reference to FIG. 4. The balloon catheter in this example is equipped with a guide tube 18 with an embedded spring-like coil 17. This coil 17 is wound closely in the axial direction, and is integrally embedded inside the guide tube 18 by insert molding or dip molding. When the coil 17 is subjected to compressive force in the axial direction, because the adjacent loops are closely spaced, there is no compression of the coil 17, and rigidity is thus high with respect to the axial direction. This allows the pushing force acting on the guide tube 18 to be transmitted more effectively to the distal end portion of the inner tube 5. The hardness of the coil 17 can also be suitably adjusted so as to resist flexing. It is preferable for this spring-like coil 17 to be composed of an X-ray impermeable material. Since rigidity, in the axial direction is thus ensured by the coil 17 in this example, if flexibility is ensured by using one of the above-mentioned elastomers as the material for the guide tube 18, then extremely high rigidity in the axial direction can be achieved while also achieving extremely good flexibility. Although not shown in the figure, in the example illustrated in FIG. 3, it is also possible for the coil 17 of this example to be embedded inside the guide tube 14, and if the coil 17 is made of an X-ray impermeable material, the above-mentioned X-ray impermeable marker 16 can be omitted. The rest of the structure is the same as in the example given above, and the same structural components are labeled with the same numbers, and will not be described again.

Before it became common practice to leave a stent in place after the dilation of a constriction, a balloon was inflated at a pressure of around 8 atm. Now that stents are being used, however, a pressure of 14 to 18 atm must be applied to the balloon in order to open up the stent. Stretching in the longitudinal direction of the balloon was not a serious problem at a pressure around 8 atm, but at a pressure of 14 atm or higher, as explained in "Background Art" above (see FIGS. 7 to 10), the stretching of the inner tube that accompanied extension of the balloon was a problem.

Therefore, balloons have needed to have better pressure resistance since the advent of stents, and the materials of which they are made have been thermoplastic elastomers exhibiting a property whereby the balloon diameter increases somewhat through extension under pressure, such as polyamide elastomers, polyurethane elastomers, and polyester elastomers, or a material such as PET with which there is little change in diameter when the pressure rises. However, although a balloon composed of PET or the like (generally called a non-compliant balloon) does have good pressure resistance, it lacks flexibility when wrapped, and it is difficult to rewrap once it has been inflated, among other drawbacks. Therefore, the above-mentioned thermoplastic elastomers are most often used for balloon materials.

A balloon composed of one of the above thermoplastic elastomers increases in diameter somewhat as the pressure rises, but at the same time it also extends in the lengthwise direction. The percentage of elongation in the lengthwise direction will vary with the type of thermoplastic elastomer and the film thickness of the balloon, but with an ordinary balloon the elongation is 3 to 8% at a pressure of 14 atm, and about 5 to 10% at a pressure of 18 atm. Therefore, although a balloon composed of one of these thermoplastic elastomers does extend in the lengthwise direction under pressure, its deformation is within the range of elastic deformation, and it returns almost to its original dimensions when deflated.

For example, with a balloon made of a polyester elastomer (wall thickness: 20 μm, outside diameter when inflated: 2.5 mm, length: 23 mm), the length at a pressure of 14 atm is 24.5 mm (elongation of 6.5%), and at a pressure of 18 atm is 25 mm (elongation of approximately 8%).

With a balloon made of a polyester elastomer and having different dimensions from the above-mentioned balloon (wall thickness: 18 μm, outside diameter when inflated: 3.0 mm, length: 25 mm), the length at a pressure of 14 atm is 27 mm (elongation of approximately 8%), and at a pressure of 18 atm is 27.5 mm (elongation of approximately 10%).

Meanwhile, a material such as HDPE (High-Density PolyEthylene) is often used for the inner tube that constitutes the guide wire lumen because of the importance assigned to good slip properties with the guide wire. With an inner tube made of HDPE, however, the range of elastic deformation is only about 2% (about 3% at best), and this range is too narrow.

Thus, the difference between the elongation of the balloon in a pressurized state and the range of elastic deformation of this inner tube leads to stretching of the inner tube due to plastic deformation. For instance, with a balloon catheter with the conventional structure shown in FIG. 7 (overall balloon length: 25 mm), if we assume that the range of elastic deformation of the inner tube is 2% and that the elongation of the balloon in the lengthwise direction at a pressure of 18 atm is 10%, then the stretching of the inner tube restrained at the distal end of the outer tube and the distal end of the balloon is about (10%−2%)×25 mm=2 mm. This 2 mm elongation of the inner tube adversely affects the rewrapping of the balloon.

In contrast, with the balloon catheter pertaining to the present invention and shown in FIG. 2 (overall catheter shaft length: 1350 mm, overall balloon length: 25 mm), if we assume that the elongation of the balloon in the lengthwise direction at a pressure of 18 atm is 10% (with the ends of the catheter shaft restrained by the branched hub and the distal end portion of the balloon), then the elongation of the inner tube is (10%×25 mm/1350 mm)×100=0.19%. This 0.19% elongation is within the range of elastic deformation of the inner tube, and when the balloon is inflated and then deflated, the inner tube will return to its original dimensions.

When the overall balloon length is 25 mm and the elongation of the balloon in the lengthwise direction at a pressure of 18 atm is 10% (2.5 mm of elongation), then the restraint length (the length between the two points where the inner tube is restrained) at which the inner tube is within its range of elastic deformation is 125 mm (range of elastic deformation of 2%) or 83 mm (range of elastic deformation of 3%). Therefore, the inner tube may be joined to the inner wall surface of the outer tube at a location at least 125 mm, and preferably at least 150 mm just to be sure, to the proximal side from the distal end joint (the proximal end portion of the sleeve 7 on the distal side of the balloon 3 in FIG. 2, etc.). In other words, if a restraint length of at least 150 mm can be ensured at the distal end portion of the catheter shaft for the inner tube, then the object of the present invention can be achieved, which is to prevent the stretching of the inner tube that accompanies balloon elongation.

The following benefits (A) to (D) can be realized with the balloon catheter pertaining to the present invention. (A) The inner tube is prevented from slackening after balloon inflation, which improves the rewrapping of the balloon and allows the catheter to pass through afflicted sites more easily on the second and subsequent times. (B) Discontinuity in rigidity in the proximity of the joint between the balloon and the distal end portion of the outer tube can be lessened, which reduces the breakage of the outer tube distal end portion which tends to occur during handling of the catheter and replacement of the guide wire. (C) The hardness of the outer tube distal end portion can be freely adjusted by adjusting the wall thickness and material of the guide tube. (D) The pushing force applied from the proximal side of the catheter shaft can be transmitted better to the distal end portion by employing a structure in which the guide tube distal end butts up against the distal end portion of the balloon or the X-ray impermeable marker.

Figure 11:
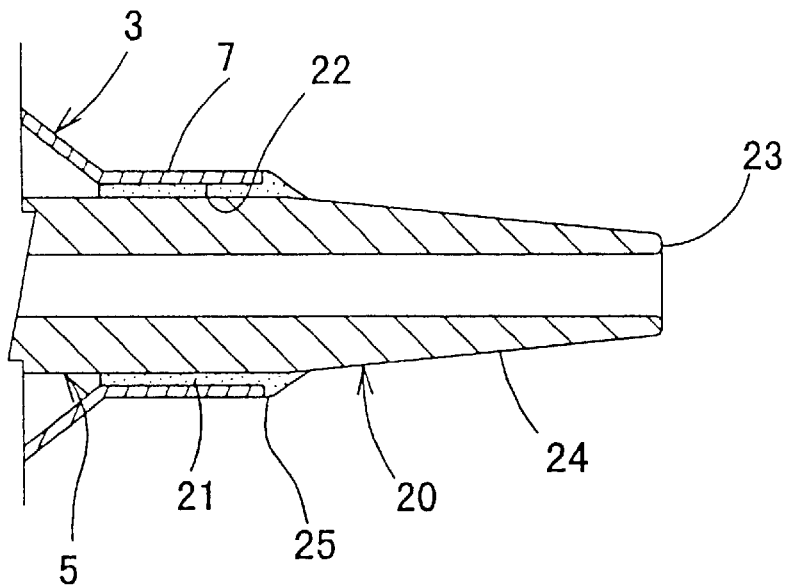
FIG. 11 is an enlarged cross section of the main components in an embodiment of the distal end tip pertaining to the present invention.

An embodiment of the distal end tip 10 pertaining to the present invention will now be described in detail. FIG. 11 is an enlarged cross section of the distal end tip 20 pertaining to the present invention. The distal end of the inner tube 5 that constitutes the guide wire lumen sticks out to the distal side from the sleeve 7 on the proximal side of the balloon 3, and the inner tube 5 and the inner peripheral surface of the distal side sleeve 7 are coaxially joined using an adhesive agent 21. The distal end tip 20 is formed in a pointed taper shape. In the distal end taper portion 24 formed up to the catheter most distal end, in which the thickness of the walls of the balloon 3 continuously decreases from the proximity of the most distal end of the joint 22 between the balloon 3 and the inner tube 5 (hereinafter referred to as the distal end-side balloon joint 22), the average thickness reduction gradient thereof is set between 6 and 60 μm/mm, the length from the distal end of the distal end-side balloon joint 22 to the catheter most distal end is set between 3 and 10 mm, and the wall thickness of the most distal end portion 23 of the distal end tip 20 is set between 10 and 50 μm. By covering the most distal end portion of the joint 22 with part of the adhesive agent layer 21 interposed between the joint 22 and the inner tube 5, the step is eliminated, which forms the distal end taper portion 24 continuously from the distal end portion of this joint 22 to the most distal end portion 23 of the distal end tip 20. The outermost diameter portion 25 of the adhesive agent layer 21 is the starting point for specifying the average thickness reduction gradient of the distal end taper portion 24.

The method for manufacturing the balloon catheter shown in FIG. 11 will now be briefly described. First, to form the distal end taper portion 24, a mandrel is inserted in the inner tube 5 and the inner tube 5 is locally heated in this state. Both ends of this heated portion are clamped and a tensile force applied, which stretches this portion to a specific length and reduces its diameter. This constricted portion is then cut so that the length of the distal end taper portion 24 will be 3 to 10 mm. The external shape of this distal end taper portion 24 is not limited to a simple taper that is linear in the axial direction, and stretching usually results in a concave shape like that of an exponential function curve, although conversely the shape may be a curve that bulges out from the straight line connecting the distal end portion and proximal end portion of the distal end taper portion 24. In any case, the wall thickness of the distal end taper portion 24 must be continuously reduced from the proximal end portion to the most distal end portion. The cut surface that becomes the most distal end portion 23 of the distal end taper portion 24 is chamfered by a suitable working means, such as filing, cutting, or local heating. Then, the distal end-side balloon joint 22 is bonded to the outer peripheral surface on the proximal side from the distal end taper portion 24 of the inner tube 5 that has undergone the above working, the distal end portion of the joint 22 is covered with part of the adhesive agent layer 21, and the external shape thereof is pointedly tapered so as to be continuous with the distal end taper portion 24. The inner tube 5 is inserted into the outer tube 4, and the distal end portion of the outer tube 4 is bonded to the joint 6 on the proximal side of the balloon 3 to complete the catheter shaft 1. The working of the distal end taper portion 24 of the inner tube 5 may also be performed after the inner tube 5 and the balloon 3 have been joined.

Figure 12:
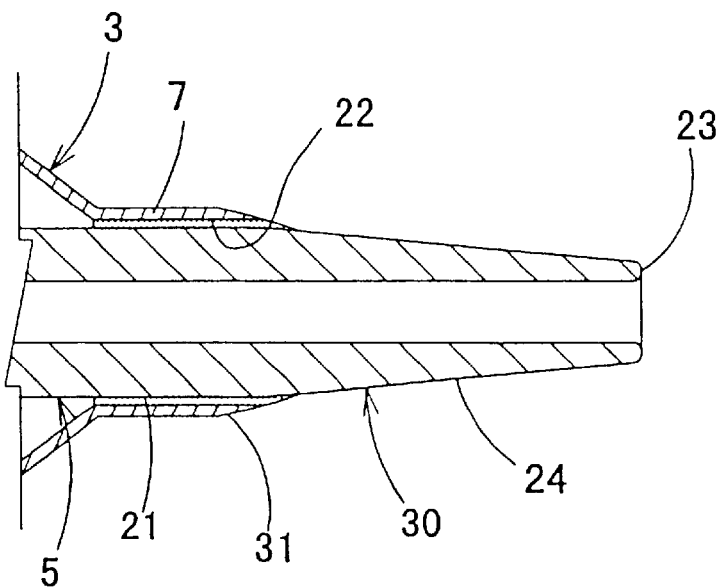
FIG. 12 is an enlarged cross section of the main components in another embodiment of the distal end tip pertaining to the present invention.

FIG. 12 illustrates an embodiment of another distal end tip 30. The step from the distal end tip 30 is eliminated by forming a pointed taper portion 31 all the way around the distal end portion of the sleeve 7 on the distal side of the balloon 3, and continuously (smoothly) forming the exposed portion of the adhesive agent layer 21 from the taper portion 31 to the distal end taper portion 24.

The method for manufacturing a balloon catheter equipped with this distal end tip 30 will now be briefly described. First, the unworked inner tube 5 is inserted in the distal end-side balloon joint 22 of the balloon 3, and the distal end portion of the inner tube 5 is allowed to protrude sufficiently from this joint 22. The inner tube 5 and the joint 22 are bonded in this state, after which local abrasion is performed on the distal end portion of the joint 22 to form the taper portion 31. Next, the portion of the inner tube 5 protruding to the distal end side beyond the joint 22 and which is near the distal end portion of the taper portion 31 is locally heated, and the proximal end portion of the distal end-side balloon joint 22 of the balloon 3 and the distal end portion of the inner tube 5 are clamped and subjected to a tensile force, which stretches this portion to a specific length and reduces its diameter. This constricted portion of the inner tube 5 is then cut so as to form the distal end taper portion 24 in a length of 3 to 10 mm. This stretching forms the distal end taper portion 24 continuously with the taper portion 31 on the inner tube 5. The cut surface that becomes the most distal end portion 23 of the distal end taper portion 24 is chamfered by a suitable working means as above. The working of the distal end taper portion 24 of the inner tube 5 and the working of the taper portion 31 in the distal end portion of the distal end-side balloon joint 22 may comprise stretching by local heating and local abrasion, respectively, prior to the bonding of the balloon 3 and the inner tube 5, after which the inner tube may be cut to a suitable length and the two bonded.

It is preferable to use the adhesive agent pertaining to the present invention (discussed below) as the adhesive agent used to bond the balloon 3 to the inner tube 5, and the balloon 3 to the outer tube 4.

In this embodiment, an adhesive agent was used to join the balloon 3 to the inner tube 5 and the outer tube 4, but a fusion means may be used instead of an adhesive agent in the present invention.

Figure 13:
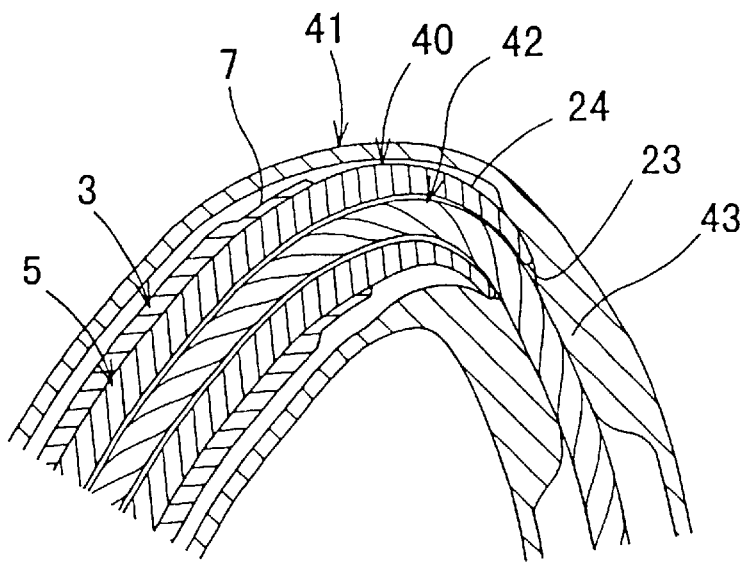
FIG. 13 is a simplified partial cross section illustrating how the distal end portion of the balloon catheter pertaining to the present invention advances into a highly curved blood vessel and works its way into a constriction.
Figure 14:
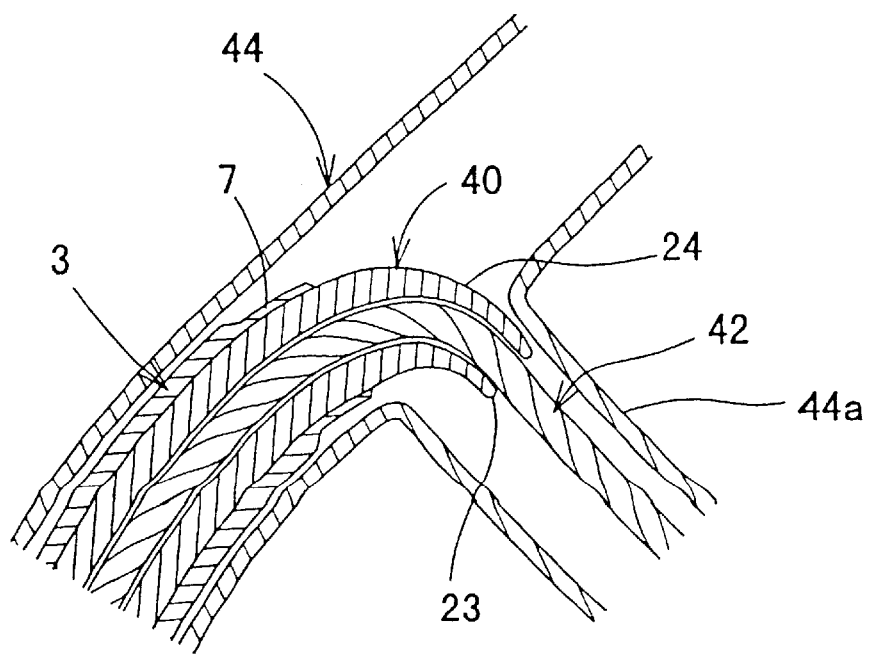
FIG. 14 is a simplified partial cross section illustrating how the distal end portion of the balloon catheter pertaining to the present invention works its way into a branched blood vessel.

With a balloon catheter produced in this manner, as shown in FIG. 13, because of the pointed taper shape of the distal end tip 40, the catheter is able to conform to the guide wire through a blood vessel 41 with a high degree of curvature, and is able to proceed smoothly from the distal end taper portion 24, and even at a severe constriction 43, the guide wire 42 can be guided through this constriction 43 and the wrapped balloon 3 located at this constriction 43. Also, with the balloon catheter of the present invention, as shown in FIG. 14, even when the balloon 3 is moved into a branched blood vessel 44*a* that branches off from the blood vessel 44 at a sharp angle, such as 90 degrees, the balloon 3 can still conform to the guide wire 42 inserted into the branched blood vessel 44*a*, and proceed smoothly from the distal end taper portion 24.

Specific working examples of the distal end tip pertaining to the present invention will now be given, and the ability of the balloon catheter to conform to the guide wire and pass smoothly through constrictions will be described.

WORKING EXAMPLES AND COMPARATIVE EXAMPLES

The basic structure in the working and comparative examples is as follows. A tube (inner tube) used as a guide wire lumen with an inside diameter of 0.40 mm and an outside diameter of 0.56 mm was molded by extrusion molding using high-density polyethylene (HDPE) ("HY540," made by Mitsubishi Chemical). Also, a balloon composed of a balloon portion with a diameter of 2.5 mm and a wall thickness of 20 μm, and distal side and proximal side sleeves with an outside diameter of about 0.76 mm was molded by extrusion molding using "Hytrel 7277" (made by Toray DuPont). A two-liquid normal temperature curing type of adhesive agent ("Coronet 4403/Nippolan 4235," made by Nippon Polyurethane Industry) was used as the adhesive agent for joining the inner tube and balloon. This inner tube was joined with an outer tube composed of nylon 12 and having an inside diameter of 0.70 mm and an outside diameter of 0.86 mm so as to form the above-mentioned double-tube structure, and the various members were assembled as shown in FIG. 1. A stainless steel mandrel with an outside diameter of approximately 0.40 mm was inserted into the hollow part of the inner tube, and the area around the joint between the inner tube and the sleeve on the distal side of the balloon was stretched to a specific length while being heated to approximately 100° C. After this, the stretched and thinned portion was cut to a specific length, forming a distal end tip. The balloon portion was wrapped in a C-shaped configuration, and creases were made with heat, thereby producing the samples of the working and comparative examples.

The samples of Working Examples 1 to 3 were produced such that the distal end tips had mutually different shapes as shown in Table 1 below by adjusting the stretching length and heating conditions for the inner tube. Comparative Examples 1 and 2 were also produced by the same method.

The samples of Working Examples 4 and 5 were produced such that the taper portion 31 was formed on the distal end portion of the joint 22 as shown in FIG. 12, and the shapes of the distal end tips were mutually different. Comparative Examples 4 and 5 were also produced by the same method.

The sample of Comparative Example 3 was produced by adjusting the outside diameter of the distal-side sleeve to about 0.86 mm at the stage of forming the balloon.

The dimensions of the distal end tips in the above Working Examples 1 to 5 and Comparative Examples 1 to 5 are given in Table 1 below.

TABLE 1

| Type of sample | Average thickness reduction gradient | Distal end tip length | Tube wall thickness at tip most distal end portion |
| --- | --- | --- | --- |
| Working Ex. 1 | 60 μm/mm | 3 mm | 10 μm |
| Working Ex. 2 | 40 μm/mm | 4 mm | 20 μm |
| Working Ex. 3 | 25 μm/mm | 6 mm | 30 μm |
| Working Ex. 4 | 10 μm/mm | 7 mm | 40 μm |
| Working Ex. 5 | 6 μm/mm | 10 mm | 50 μm |
| Comp. Ex. 1 | 60 μm/mm | 3 mm | 5 μm |
| Comp. Ex. 2 | 60 μm/mm | 2 mm | 60 μm |
| Comp. Ex. 3 | 70 μm/mm | 3 mm | 20 μm |
| Comp. Ex. 4 | 6 μm/mm | 10 mm | 60 μm |
| Comp. Ex. 5 | 6 μm/mm | 15 mm | 20 μm |

The various samples will be briefly described. The sample in Working Example 1 had an average thickness reduction gradient for the distal end taper portion at the maximum value, the sample in Working Example 2 had an average thickness reduction gradient at the upper end of the favorable range, the sample in Working Example 3 was produced under the most favorable conditions, the sample in Working Example 4 had an average thickness reduction gradient at the lower end of the favorable range, and the sample in Working Example 5 had an average thickness reduction gradient for the distal end taper portion at the minimum value. The sample in Comparative Example 1 had an average thickness reduction gradient at the maximum value, but the distal end walls were too thin, the sample in Comparative Example 2 had an average thickness reduction gradient at the maximum value, but the distal end tip was too short, the sample in Comparative Example 3 had an average thickness reduction gradient over the maximum value, the sample in Comparative Example 4 had an average thickness reduction gradient at the minimum value, but the distal end walls were too thick, and the sample in Comparative Example 5 had an average thickness reduction gradient at the minimum value, but the distal end tip was too long.

Test Model 1

Figure 15:
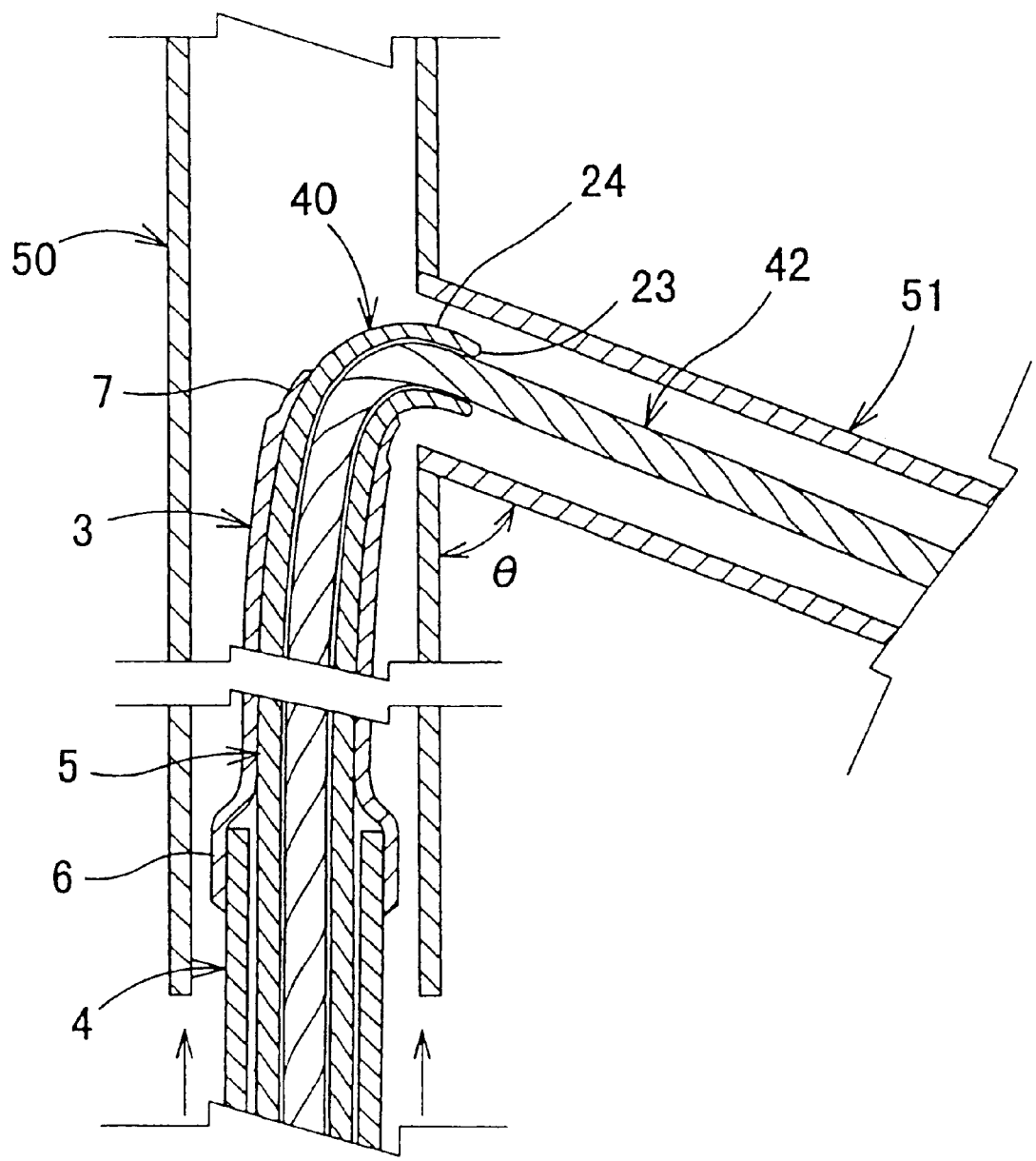
FIG. 15 is a simplified cross section illustrating a model for testing conformity to the guide wire.

The first test model to which the above samples were subjected was used to evaluate their conformity to the guide wire. As shown in FIG. 15, a hole was made in the side of a glass tube 50 with an inside diameter of 4 mm, and a urethane tube 51 with an inside diameter of 3.5 mm was set into this glass tube 50 such that there was no step on the inside (the rest of the numbering in the figure is the same as that used for the balloon catheter in FIG. 13). The guide wire 42 was threaded into the glass tube 50 and through the tube 51, and the angle θ formed by the glass tube 50 and the urethane tube 51 was varied while the balloon catheter was checked to see up to what angle it would conform to the guide wire 42. "Athlete Soft" (made by Lifeline Japan) was used for the guide wire 42. These results are given in Table 2 below.

TABLE 2

| | Angle (θ) formed by glass tube and urethane tube | | | | | | | |
|---|---|---|---|---|---|---|---|---|
| | 90 deg | 80 deg | 70 deg | 60 deg | 50 deg | 40 deg | 30 deg | 20 deg |
| W.E. 1 | ○ | ○ | ○ | Δ | Δ | Δ | Δ | Δ |
| W.E. 2 | ○ | ○ | ○ | ○ | ○ | ○ | ○ | ○ |
| W.E. 3 | ○ | ○ | ○ | ○ | ○ | ○ | ○ | ○ |
| W.E. 4 | ○ | ○ | ○ | ○ | ○ | ○ | ○ | ○ |
| W.E. 5 | ○ | ○ | ○ | ○ | ○ | ○ | ○ | ○ |
| C.E. 1 | | ○ | | Δ | | Δ | | Split at distal end |
| C.E. 2 | ○ | ○ | × | × | × | × | × | × |
| C.E. 3 | ○ | ○ | Δ | Δ | × | × | × | × |
| C.E. 4 | ○ | ○ | ○ | ○ | ○ | ○ | ○ | ○ |
| C.E. 5 | ○ | ○ | ○ | ○ | ○ | ○ | ○ | ○ |

In Table 2, "Δ" indicates that the most distal end portion 23 of the distal end taper portion 24 had a somewhat trumpet-like shape, "×" indicates that the guide wire 42 was bent, and "○" indicates that there was no problem whatsoever.

It can be seen from the results in Table 2 that the samples with a large average thickness reduction gradient were inferior in terms of conforming to the guide wire. This is believed to be because the rigidity changes abruptly at a distal end tip that is short. With those samples that had a large average thickness reduction gradient and had thick walls in the distal end portion, it can be seen that breakage of the guide wire tended to occur in curved sections. On the other hand, those samples with a small average thickness reduction gradient received high marks for conformity to the guide wire. With the sample with thin walls at the most distal end portion, breakage occurred when the tip tried to conform to a curved section.

Test Model 2

Figure 16:
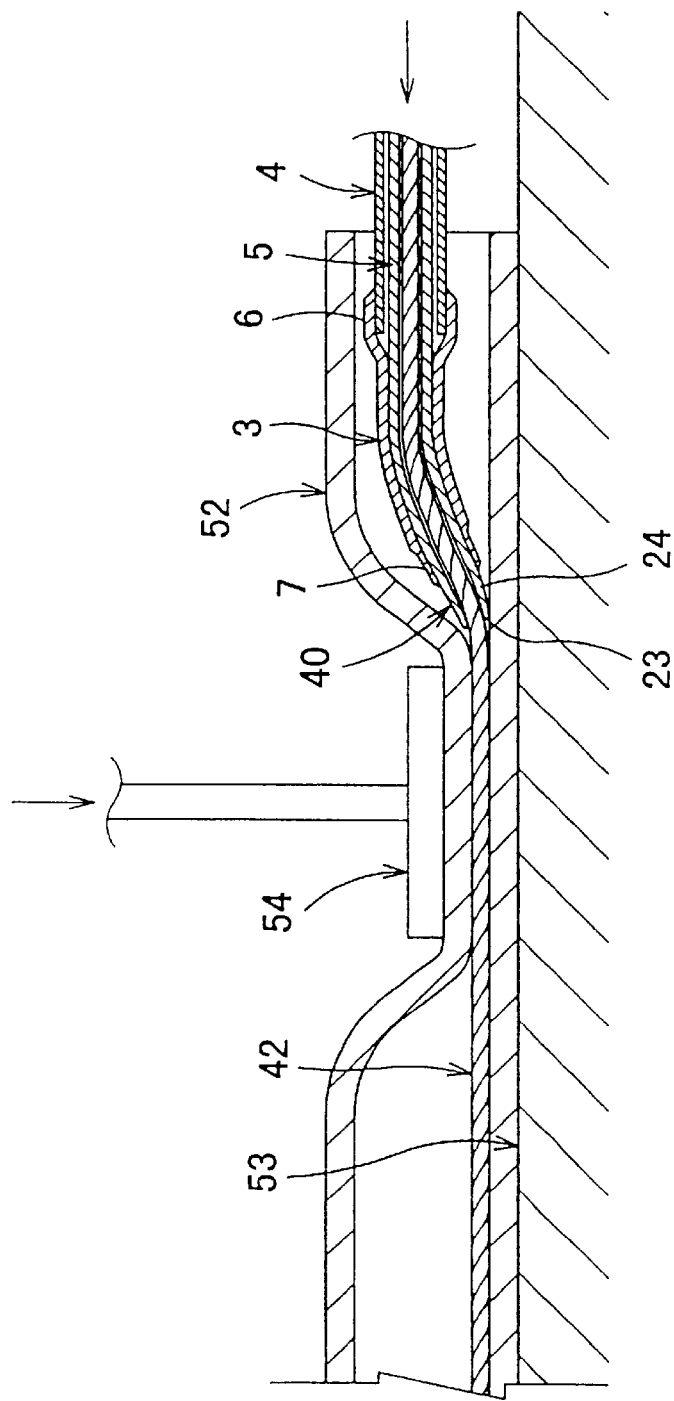
FIG. 16 is a simplified cross section illustrating a model for testing ease of passage through a constriction.

The second test model to which the above samples were subjected was used to evaluate the ease of passage of the distal end tip. The test model shown in FIG. 16 was used. This test model featured a silicone tube 52 with an inside diameter of 2 mm and an outside diameter of 3 mm. The guide wire 42 was placed in a flat test stand 53 after having been inserted into the tube 52, a force of 700 gf was applied to the tube 52 from above by a pressing disk 54 having a diameter of 16 mm, which flattened part of the tube 52 and formed a simulated constriction. The sample was threaded into this constriction and evaluated for how well it passed through. A portion on the proximal side of "Athlete Soft" (made by Lifeline Japan) was used for the guide wire. In this evaluation, the entire distal end tip portion was viewed as having passed through upon entering the portion under the load. These results are given in Table 3 below.

TABLE 3

| | Passed or not | Remarks |
|---|---|---|
| Working Ex. 1 | passed | good passage |
| Working Ex. 2 | passed | good passage |
| Working Ex. 3 | passed | good passage |
| Working Ex. 4 | passed | some resistance at first, but no problem |
| Working Ex. 5 | passed | resistance at first, but no problem |
| Comp. Ex. 1 | passed | passage good, but most distal end portion accordioned |
| Comp. Ex. 2 | did not pass | most distal end portion would not enter |
| Comp. Ex. 3 | passed | high resistance at bonded portion of balloon |
| Comp. Ex. 4 | did not pass | most distal end portion would not enter |
| Comp. Ex. 5 | passed part way | entered part way, but high resistance; shaft joined to proximal side of balloon broke under pressing force |

It can be seen from the results in Table 3 that the resistance to which the distal end tip is subjected increases if the distal end tip is too long. Also, if the walls of the most distal end portion of the distal end tip are too thick, snagging will occur and passage will be more difficult. It was also confirmed that accordion-like flattening in the axial direction occurs in the thin-walled portion if the walls of the most distal end portion are thin, although this varies with the load applied. Therefore, it we take into account conformity to the guide wire and ease of passage through constrictions, it is good for the distal end tip portion to have an average thickness reduction gradient of 6 to 60 μm/mm, a length of 3 to 10 mm, and a wall thickness in the most distal end portion of 10 to 50 μm. Furthermore, it is preferable for the average thickness reduction gradient of the distal end tip portion to be 10 to 30 μm/mm, the length to be 4 to 7 mm, and the wall thickness in the most distal end portion to be 20 to 40 μm.

Using the distal end tip pertaining to the present invention results in the balloon catheter distal end portion being more flexible and smaller in diameter, which improves its passage to sites where the surface resistance is high, such as in a stent, or to afflicted sites with a high degree of curvature or a high degree of difficulty.

Next, an embodiment of a preferred adhesive agent for joining the balloon 3 to the inner tube 5, and the balloon 3 to the outer tube 4 will be described. This adhesive agent must not cause any discontinuity in rigidity of the catheter shaft distal end portion due to the curing of the adhesive agent, and must have good pressure-resistance strength, as well as the flexibility required for good conformity to curved blood vessels. A preferable adhesive agent is one for which the durometer hardness (D value) indicating the state of curing is at least D16 and no more than D70, and preferably at least D30 and no more than D70.

Durometer hardness is broadly classified into two types, D hardness and A hardness, according to the measurement method. Methods for measuring this durometer hardness are given in JIS K 7215, ASTM-D2240, and elsewhere. D hardness and A hardness do not lend themselves well to simple conversion because the shape of the durometer probe, the test load, and other factors vary, but D58 is generally more or less equivalent to A100, D30 to A80, and D16 to A60. Therefore, the characteristics of the above-mentioned adhesive agent are such that the hardness after curing, in D value, will be at least D16 and no more than D70, and preferably at least D30 and no more than D70, but it can be easily inferred from the above relationship that the hardness after curing is at least A60, and preferably at least A80.

In general, when adhesive agents are classified by how they cure, the classifications include single-liquid heat curing types, water-absorption curing types, two-liquid heat curing types, two-liquid normal temperature (room temperature) curing types, and radiation curing types. Radiation curing types include UV curing and electron beam curing types.

It is important for the adhesive agent used in the present invention to have a hardness (D value) after curing that satisfies a range of at least D16 and no more than D70, and preferably at least D30 and no more than D70. The curing type is not important, but a two-liquid normal temperature (room temperature) curing adhesive agent, a UV curing adhesive agent, and a water-absorption curing adhesive agent are preferred. When a heat curing adhesive agent is used, the catheter shaft and balloon are inevitably exposed to heat during the heating required for curing. As a result, it is entirely possible that the balloon diameter will shrink, the balloon bursting pressure will decrease, and the catheter shaft will undergo thermal degradation, and these all lead to diminished balloon catheter performance, so the use of a heat curing adhesive agent is not advised. When an electron beam curing adhesive agent is used, large-scale electron beam irradiation equipment is required, which is a drawback from a cost standpoint.

It has already been mentioned that the hardness (D value) of the above-mentioned two-liquid normal temperature (room temperature) curing adhesive agent, UV curing adhesive agent, and water-absorption curing adhesive agent should be at least D16 and no more than D70, and preferably at least D30 and no more than D70, but to add to this, it is preferable for the hardness of the adhesive agent to be lower than that of the catheter shaft and the balloon. With a combination such as this, there will be no discontinuity in rigidity throughout the catheter after the curing of the adhesive agent, nor will the flexibility of the distal end tip be lost.

However, when the hardness of the adhesive agent needs to be higher than that of the catheter shaft and the balloon to ensure adequate pressure resistance and strength after curing, or for some other reason, the adhesive agent with the lowest feasible hardness should be selected.

There are no particular restrictions on the composition or chemical structure of the above-mentioned two-liquid normal temperature (room temperature) curing adhesive agent, UV curing adhesive agent, and water-absorption curing adhesive agent. Specifically, a common urethane, epoxy, or silicone type of adhesive agent comprising a mixture of a main component and a curing agent can be used as a two-liquid room temperature curing adhesive agent, and a cyanoacrylate-based adhesive agent, a single-liquid curing urethane adhesive agent, or the like can be used as a water-absorption curing adhesive agent.

Figure 17:
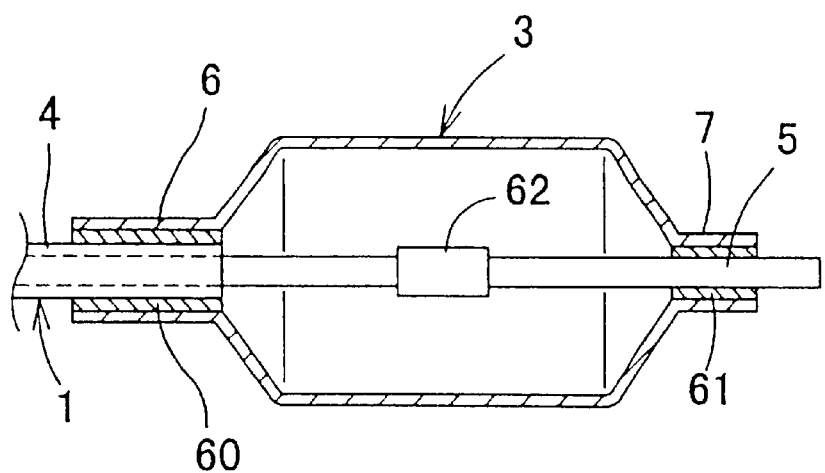
FIG. 17 is an enlarged cross section of the main components in an embodiment of the method for applying the adhesive agent pertaining to the present invention.
Figure 18:
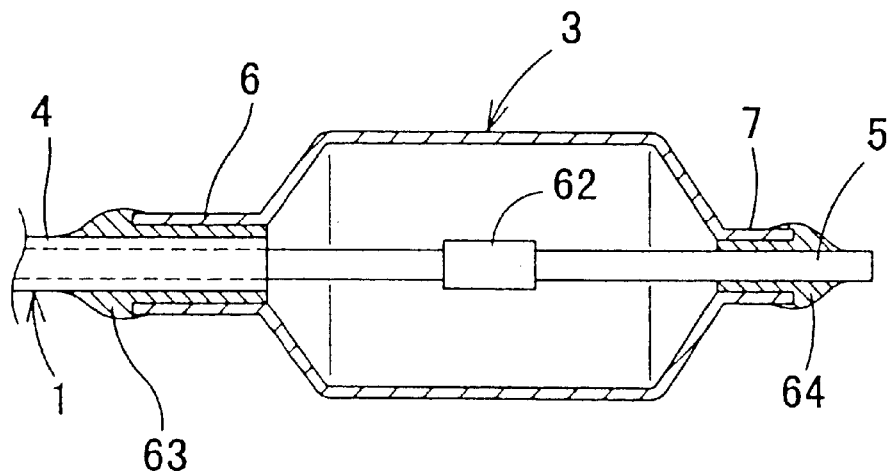
FIG. 18 is an enlarged cross section of the main components in another embodiment of the method for applying the adhesive agent pertaining to the present invention.

There are no particular restrictions on the method for applying the adhesive agent, but it is preferable for the balloon portion after bonding to be as shown in FIGS. 17 and 18, and particularly as in the above-mentioned FIGS. 11 and 12. In FIG. 17, 4 is the outer tube of a catheter shaft 1 comprising a double-tube, 5 is the inner tube of the catheter shaft 1 comprising a double-tube, 3 is a balloon, 60 is an adhesive agent applied to the joined portions of the outer tube 4 and the sleeve 6 on the proximal side, 61 is an adhesive agent applied to the joined portions of the inner tube 5 and the sleeve 7 on the distal side, and 62 is an X-ray impermeable marker provided to the inner tube 5 in the interior of the balloon 3. FIG. 18 shows a structure in which adhesive agents 63 and 64 have been built up on the sleeves 6 and 7 of the balloon 3, which reduces the discontinuity in rigidity and the step between the inner tube 5 and outer tube 4 and the balloon 3.

The adhesive agent may be applied by a method in which a suitable amount of adhesive agent is used to coat the joined portions of the outer tube 4 and inner tube 5 of the catheter shaft 1 ahead of time, after which the catheter shaft and the balloon are assembled, or the catheter shaft and balloon may be assembled and the adhesive agent then allowed to flow into the joined portions of the outer tube 4 and inner tube 5 of the catheter shaft 1. The effect of the present invention is not limited by using another method besides the above to apply the adhesive agent.

A preferred embodiment of a balloon catheter assembled using the above-mentioned adhesive agent will now be described.

Working Example 6

An inner tube with an inside diameter of 0.42 mm and an outside diameter of 0.56 mm was molded by extrusion molding using high-density polyethylene (HDPE) ("HY540," made by Mitsubishi Chemical; durometer hardness: D70). An outer tube with an inside diameter of 0.71 mm and an outside diameter of 0.90 mm was molded by extrusion molding using a polyamide-based elastomer ("Pebax 6333SA00," made by Toray; durometer hardness: D63). This inner tube and outer tube were coaxially disposed in the form of a double-tube to produce a catheter shaft.

A tube with an inside diameter of 0.43 mm and an outside diameter of 0.96 mm was also molded using a polyester-based elastomer ("Hytrel 7277," made by Toray DuPont; durometer hardness: D72), and this tube was blow molded to produce a balloon with an outside diameter of 3.0 mm and a wall thickness of 19 $\mu$m.

This balloon was bonded to the above-mentioned catheter shaft as shown in FIG. 17 using a UV curing adhesive agent ("3211," made by Loctite; durometer hardness: D51) to produce the sample of Working Example 6. Irradiation with ultraviolet rays (UV) was performed at 1 W/cm$^2$.

Working Example 7

Using the same catheter shaft, balloon, and UV irradiation apparatus as in Working Example 6, the balloon and catheter shaft were bonded using a UV curing adhesive agent ("9110," made by Grace; durometer hardness: D55) to produce the sample of Working Example 7.

Working Example 8

Using the same catheter shaft and balloon as in Working Example 6, the balloon and catheter shaft were bonded using a two-liquid normal temperature (room temperature) curing type of urethane-based adhesive agent ("Coronet 4403/ Nippolan 4235," made by Nippon Polyurethane Industry; durometer hardness: A97) to produce the sample of Working Example 8.

Working Example 9

Using the same catheter shaft and balloon as in Working Example 6, the balloon and catheter shaft were bonded using a water-absorption curing cyanoacrylate-based adhesive agent ("911P3," made by Toagosei Chemical Industry; durometer hardness: D30 to D60) to produce the sample of Working Example 9.

Working Example 10

Using the same catheter shaft and balloon as in Working Example 6, the balloon and catheter shaft were bonded using a two-liquid normal temperature (room temperature) curing type of epoxy-based adhesive agent ("Aron Mighty AP-400," made by Toagosei Chemical Industry; durometer hardness: A30) to produce the sample of Working Example 10.

Working Example 11

Using the same catheter shaft and balloon as in Working Example 6, the balloon and catheter shaft were bonded using a water-absorption curing cyanoacrylate-based adhesive agent ("901H3," made by Toagosei Chemical Industry; durometer hardness: D70) to produce the sample of Working Example 11.

Working Example 12

Using the same catheter shaft and balloon as in Working Example 6, the balloon and catheter shaft were bonded using a two-liquid normal temperature (room temperature) curing type of urethane-based adhesive agent ("UR0531," made by H.B. Fuller; durometer hardness: D60) to produce the sample of Working Example 12.

Working Example 13

Using the same catheter shaft, balloon, and UV irradiation apparatus as in Working Example 6, the balloon and catheter shaft were bonded using a UV curing adhesive agent ("3341," made by Loctite; durometer hardness: D27) to produce the sample of Working Example 13.

Working Example 14

Using the same catheter shaft, balloon, and UV irradiation apparatus as in Working Example 6, the balloon and catheter shaft were bonded using a UV curing adhesive agent ("202-CTH," made by Dymax; durometer hardness: A80) to produce the sample of Working Example 14.

Working Example 15

Using the same catheter shaft, balloon, and UV irradiation apparatus as in Working Example 6, the balloon and catheter shaft were bonded using a UV curing adhesive agent ("3381," made by Loctite; durometer hardness: at least A72) to produce the sample of Working Example 15.

Comparative Example 6

Using the same catheter shaft and balloon as in Working Example 6, the balloon and catheter shaft were bonded using a two-liquid normal temperature (room temperature) curing type of silicone-based adhesive agent ("RTV8112," made by GE Silicones; durometer hardness: A42) to produce the sample of Comparative Example 6.

Comparative Example 7

Using the same catheter shaft, balloon, and UV irradiation apparatus as in Working Example 6, the balloon and catheter shaft were bonded using a UV curing adhesive agent. ("128M," made by Dymax; durometer hardness: D75) to produce the sample of Comparative Example 7.

Comparative Example 8

Using the same catheter shaft and balloon as in Working Example 6, the balloon and catheter shaft were bonded using a water-absorption curing cyanoacrylate-based adhesive agent ("901H2," made by Toagosei Chemical Industry; durometer hardness: D80) to produce the sample of Comparative Example 8.

Test Model 3

Figure 19:
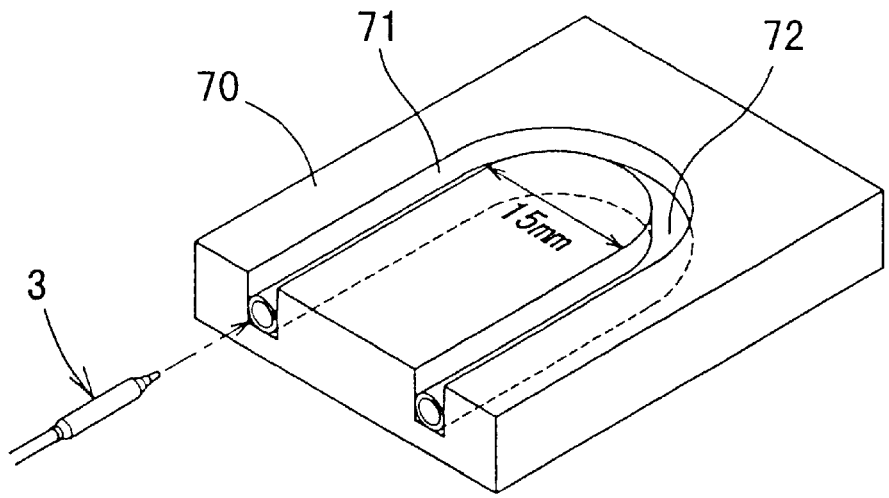
FIG. 19 is a simplified oblique view of a U-shaped simulated curved blood vessel.

The above-mentioned samples were subjected to evaluation by this test model. In this evaluation, the sample was inserted into a U-shaped simulated blood vessel plate (see FIG. 19) submerged in 37° C. physiological saline, at which point a check was made for kinks in the bonded portion on the balloon proximal side or the bonded portion on the balloon distal end side in the most curved section. These results are given in Tables 4 and 5. As shown in FIG. 19, this U-shaped simulated blood vessel plate had a U-shaped groove 71 molded into the surface of an acrylic board 70, and a polyethylene tube 72 was disposed along this U-shaped groove 71 to create a simulated blood vessel. The curved section of the U-shaped simulated blood vessel formed a semicircle with a diameter of 15 mm at the inside diameter of the tube.

The balloon portion of the sample was covered with a stainless steel pipe having an inside diameter of 3.0 mm to keep the balloon from bursting, after which physiological saline was pumped into the balloon to raise the pressure in increments of 1 atm. Each pressure level was held for 10 seconds, and the pressure at which leakage occurred from the balloon distal end-side bonded portion and the balloon proximal end-side bonded portion was measured. These pressure resistance results are given in Tables 4 and 5.

TABLE 4

| Working Example No. | Type of adhesive agent | Durometer hardness | Kinks present? | Pressure resistance (atm) |
|---|---|---|---|---|
| 6 | UV curing | D51 | no | 28.2 ± 1.9 |
| 7 | UV curing | D55 | no | 28.2 ± 2.3 |
| 8 | 2-liq. room temp. curing urethane type | A97 (equiv. D50) | no | 27.7 ± 2.7 |
| 9 | water-absorption curing cyanoacrylate type | D30–D60 | no | 27.2 ± 3.1 |
| 10 | 2-liq. room temp. curing epoxy type | D30 | no | 28.2 ± 1.9 |
| 11 | water-absorption curing cyanoacrylate type | D70 | no | 27.1 ± 1.5 |
| 12 | 2-liq. room temp. curing urethane type | D60 | no | 29.1 ± 1.2 |

TABLE 4-continued

| Working Example No. | Type of adhesive agent | Durometer hardness | Kinks present? | Pressure resistance (atm) |
|---|---|---|---|---|
| 13 | UV curing | D27 | no | 22.2 ± 2.4 |
| 14 | UV curing | A60 (equiv. D16) | no | 22.0 ± 1.7 |
| 15 | UV curing | A72+ (equiv. D23+) | no | 21.7 ± 1.6 |

TABLE 5

| Comp. Example No. | Type of adhesive agent | Durometer hardness | Kinks present? | Pressure resistance (atm) |
|---|---|---|---|---|
| 6 | 2-liq. room temp. curing silicone type | A42 (equiv. D9) | no | 12.6 ± 3.1 |
| 7 | UV curing | D75 | yes | 27.8 ± 3.2 |
| 8 | water-absorption curing cyanoacrylate type | D80 | yes | 28.5 ± 1.5 |

A balloon composed of the "Hytrel 7277" used in the above working and comparative examples has an average bursting pressure of 22.9±0.41 atm. It goes without saying that the pressure resistance of the catheter shaft and balloon bond must be over the average bursting pressure of the balloon. This is because if the balloon bond breaks at a lower pressure than the balloon bursts, there is the possibility that the balloon will remain in the blood vessel, which poses a grave danger. The results in Table 4 reveal that the pressure resistance of the bonded portions in Working Examples 6 to 12 is over the average bursting pressure of the balloon, and that there were no kinks in the catheter shaft. In other words, there was no discontinuity in rigidity in the bonded portions, and the resulting catheter shaft had sufficient pressure resistance.

Meanwhile, Working Examples 13 to 15 were the same as Working Examples 6 to 12 in that there were no kinks in the simulated curved blood vessel, but the pressure resistance of the bonded portions was below the average bursting pressure of the bonds. We can therefore conclude that there is a very high likelihood that the bonded portion will break before the balloon bursts when one of these adhesive agents is used. However, the adhesive agents used in Working Example 13 to 15 can still be used by using a balloon having an average bursting pressure that is lower than the average bursting pressure of about 16 atm in these working examples.

No kinking occurred in the sample of Comparative Example 6, but the pressure resistance of the bonded portions was extremely low. In this case, only a balloon with an extremely low pressure resistance (an average bursting pressure of only a few atmospheres) can be used, so the performance is not adequate for a balloon catheter.

Sufficient pressure resistance was obtained in Comparative Examples 7 and 8, but it can be seen that kinking occurred upon insertion into the simulated curved blood vessel. In both instances the kinks occurred in the bonded portion on the proximal side of the balloon, and one possible cause of this is that the hardness of the bonded portion on the proximal side of the balloon was so much higher than that of the material of which the outer tube was made (Pebax 6333SA00, durometer hardness: D63).

Figure 20:
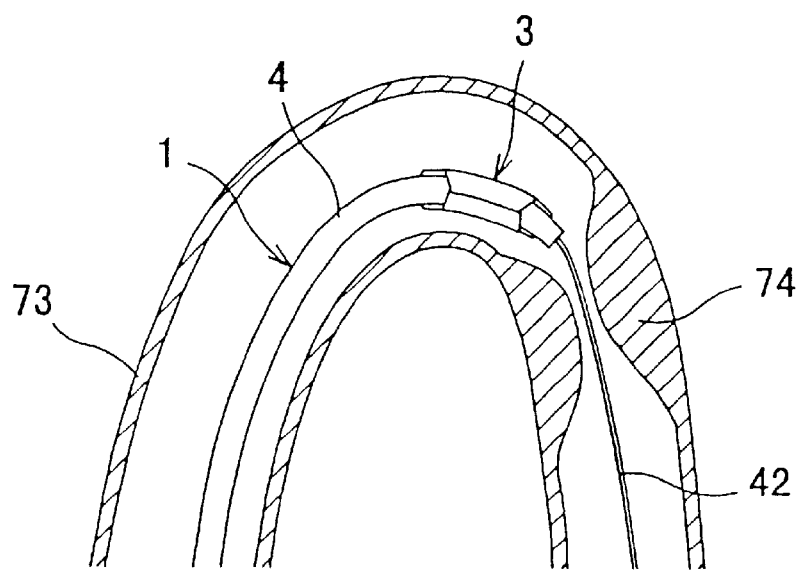
FIG. 20 is a simplified cross section illustrating how the balloon catheter pertaining to the present invention passes through a coronary artery curved section.
Figure 21:
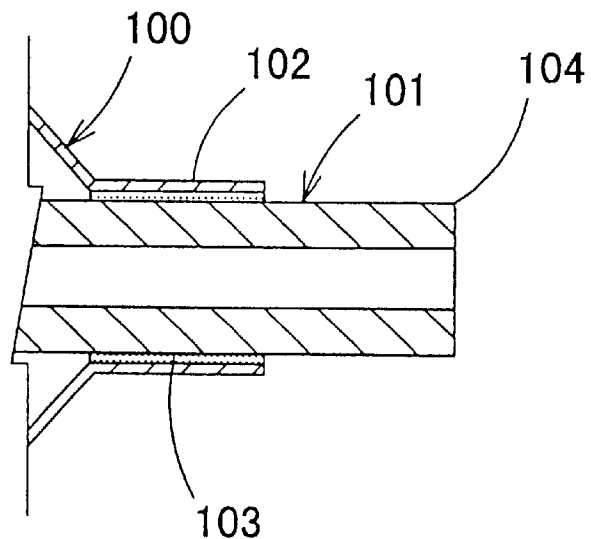
FIG. 21 is a cross section of the main components in a conventional example of a balloon catheter.
Figure 22:
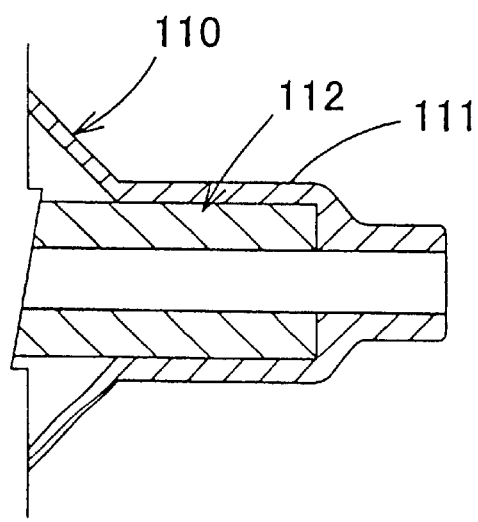
FIG. 22 is a cross section of the main components in a conventional example of a balloon catheter.
Figure 23:
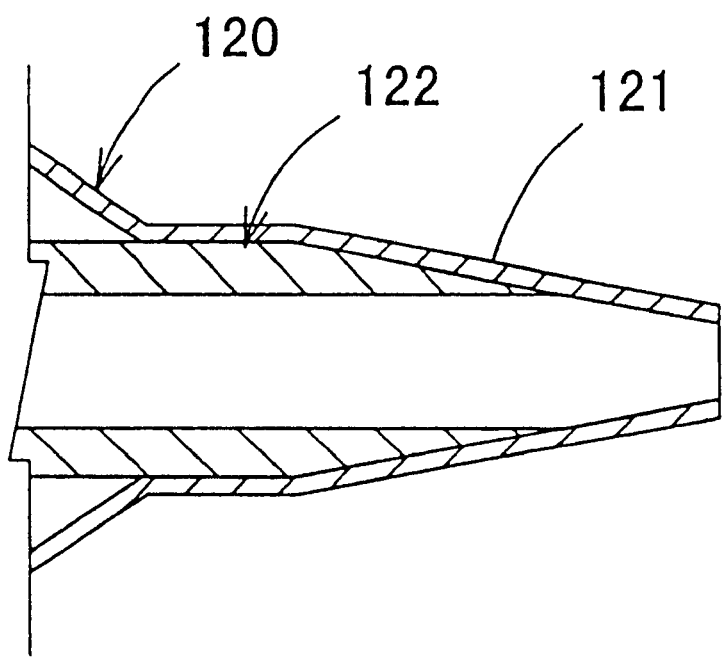
FIG. 23 is a cross section of the main components in a conventional example of a balloon catheter.
Figure 24:
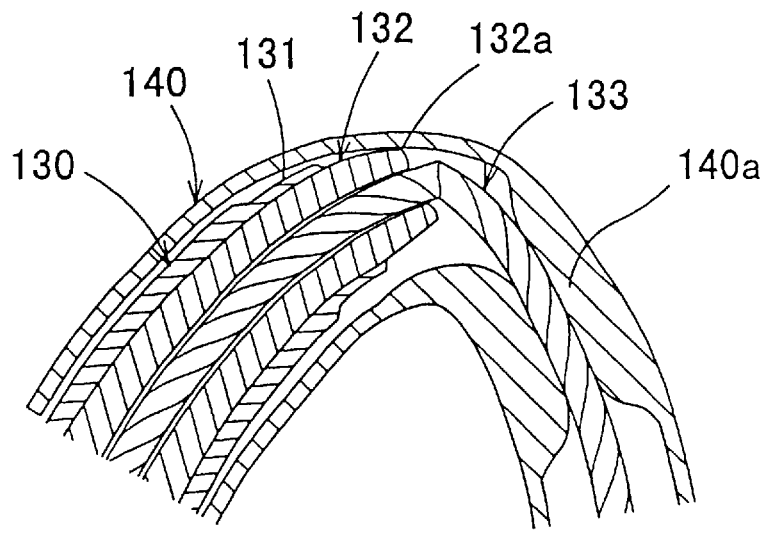
FIG. 24 is a simplified cross section illustrating the poor guide wire conformity of a conventional balloon catheter in a highly curved blood vessel.
Figure 25:
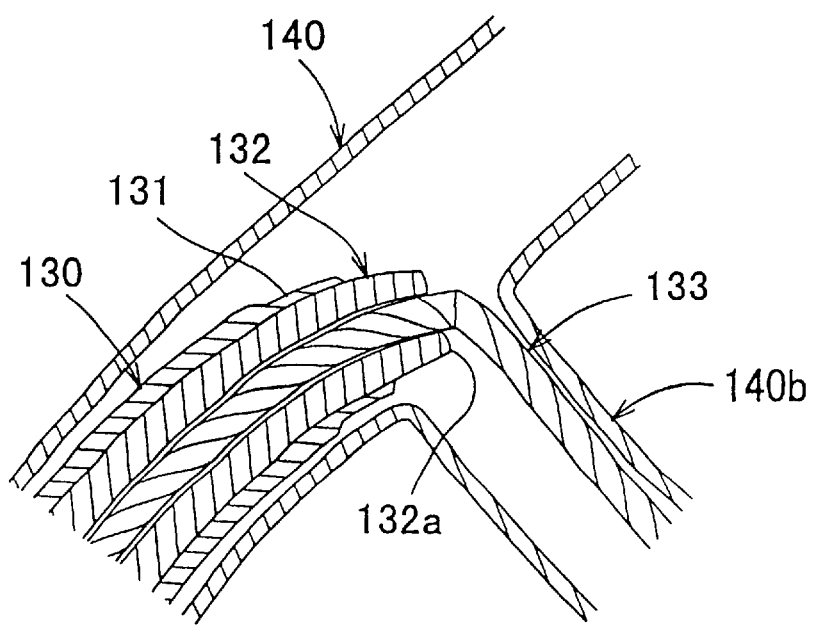
FIG. 25 is a simplified cross section illustrating the poor guide wire conformity of a conventional balloon catheter in a branched blood vessel.
Figure 26:
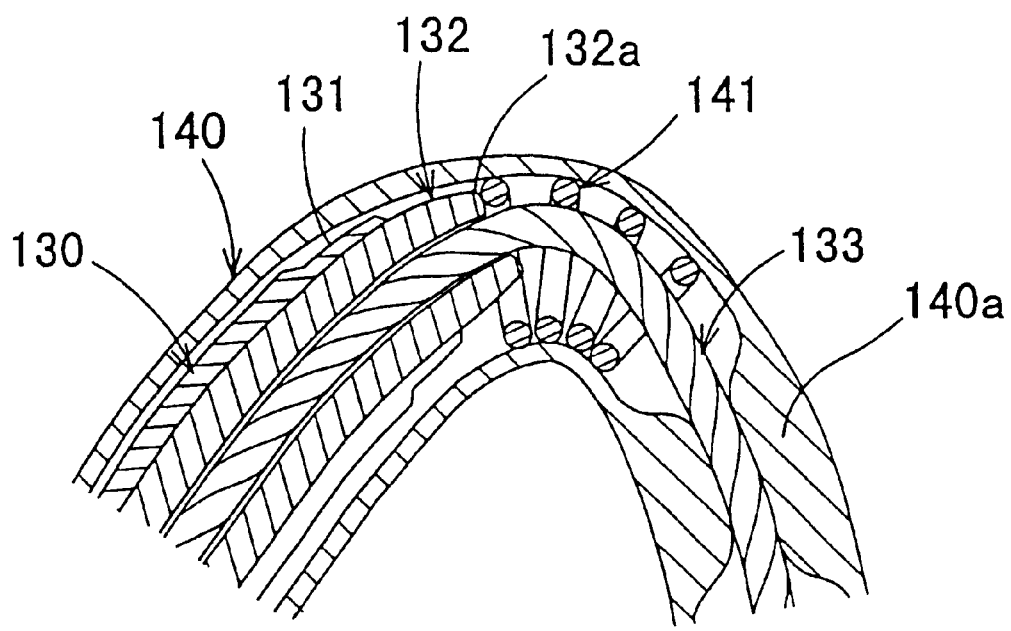
FIG. 26 is a simplified cross section illustrating the poor passage of a conventional balloon catheter when a stent is present.
Figure 27:
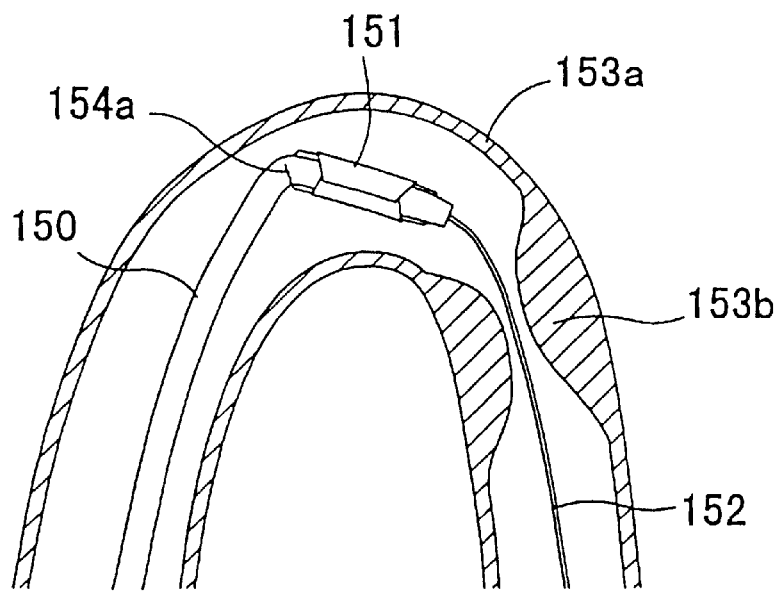
FIG. 27 is a simplified cross section illustrating how a conventional balloon catheter, in which an adhesive agent with high hardness is used to bond the balloon catheter and the balloon, becomes kinked at the bonded portion on the balloon proximal end as it passes through a coronary artery curved section.
Figure 28:
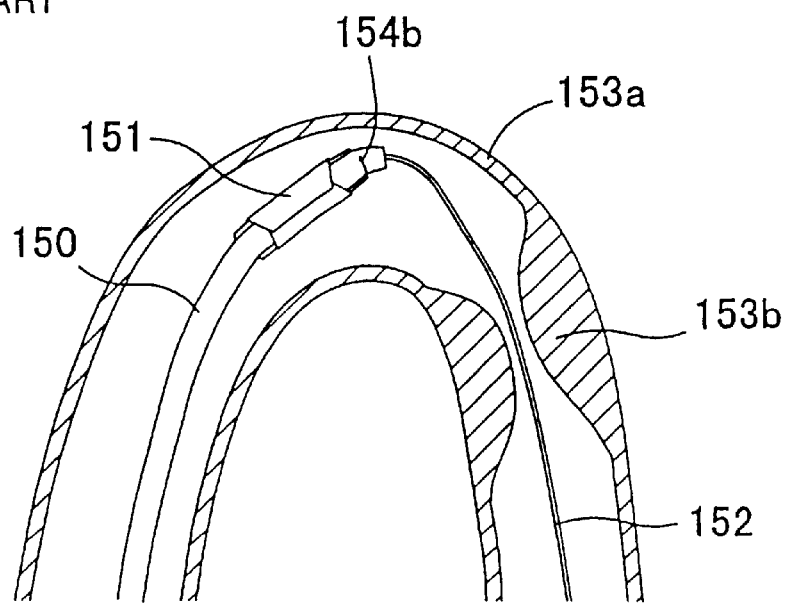
FIG. 28 is a simplified cross section illustrating how a conventional balloon catheter, in which an adhesive agent with high hardness is used to bond the balloon catheter and the balloon, becomes kinked at the bonded portion on the balloon distal end as it passes through a coronary artery curved section.

Therefore, the balloon catheters in the above working examples were flexible enough that they were able to pass through the highly curved blood vessel 73 shown in FIG. 20 without kinking, and were able to advance into the constriction 74. Naturally, the balloon bonded portions had enough pressure resistance for the balloon 3 to be inflated.

With the balloon catheters pertaining to the present invention in which the above-mentioned adhesive agents were used, the flexibility of the catheter shaft, balloon, and distal end tip can be easily maintained by controlling the durometer hardness after the curing of the adhesive agent, and as a result, the catheter will conform better to curved blood vessels, and insertion of the catheter into constrictions is easy.

Next, a preferred embodiment of the balloon pertaining to the present invention will be described. This balloon is composed of a polymer alloy including a styrene-based thermoplastic elastomer with excellent miscibility and easy resin modification. It is thus possible to obtain a balloon that has excellent flexibility, is easily wrapped, and has good wrapping shape retention. This is advantageous in the manipulation and use of the balloon catheter inside blood vessels. The term "polymer alloy" is used here in a sense that encompasses polymer blends, block and graft macromolecules, and IPNs (Interpenetrating Polymer Networks).

There are no particular restrictions on the above-mentioned styrene-based thermoplastic elastomer, but a functional group-endowed thermoplastic elastomer can be used to particularly good advantage, and the use of this elastomer affords better polymer alloy adhesion and miscibility with other materials, and yields a balloon that is safer to use. This material also has excellent coatability, so the various coatings required for a balloon catheter can be applied freely, and the holding capacity thereof is also excellent. The above-mentioned functional group-endowed thermoplastic elastomer is preferably one which has been endowed with polar groups or acid modified through a reaction with maleic anhydride or a silicon compound, and the acid value thereof should be suitably selected according to miscibility with other materials.

A hydrogenated styrene-based thermoplastic elastomer, produced by modifying the properties of a styrene-based thermoplastic elastomer through hydrogenation, is preferable as the above-mentioned styrene-based thermoplastic elastomer because it has superior temperature characteristics and durability.

Styrene-based thermoplastic elastomers are softer than other thermoplastic elastomers, and can have a wide range of properties, all the way down to extremely low hardness, so the inflation characteristics of the balloon can be controlled over a greater range by using one of these elastomers as a constituent component of the polymer alloy that makes up the balloon. The effect is pronounced even at very low added amounts, and these elastomers do not decrease the strength of the polymer alloy, so it is possible to obtain a balloon that is thin-walled, has high pressure resistance, and also has high inflation characteristics.

An example of a favorable polymer alloy is one composed of a combination of a styrene-based thermoplastic elastomer and a polyester resin, polyester-based thermoplastic elastomer, polyamide resin, polyamide-based thermoplastic elastomer, polyurethane, polyphenylene ether, or other such relatively hard macromolecular material with a high modulus of elasticity. There are no particular restrictions on the amount in which the styrene-based thermoplastic elastomer is contained, and the amount may be suitably selected as dictated by the inflation characteristics required of the balloon, but since the bursting strength of the balloon decreases as the proportion of styrene-based thermoplastic elastomer in the polymer alloy increases, it is preferable for this amount to be 1 to 30 wt %, with 5 to 30 wt % being even better. An example of a favorable combination is a polymer alloy containing 5 to 30 wt % styrene-based thermoplastic elastomer and 70 to 95 wt % polyethylene terephthalate.

Other favorable polymer alloys are combinations of a styrene-based thermoplastic elastomer and two or more relatively hard macromolecular materials with a high modulus of elasticity, such as a polyester resin, polyester-based thermoplastic elastomer, polyamide resin, polyamide-based thermoplastic elastomer, polyurethane, or polyphenylene ether, as well as polymer alloys composed of a combination of a styrene-based thermoplastic elastomer, at least one type of relatively hard macromolecular material with a high modulus of elasticity, such as a polyester resin, polyester-based thermoplastic elastomer, polyamide resin, polyamide-based thermoplastic elastomer, polyurethane, or polyphenylene ether, and a polyolefin. Here again, the amount in which the styrene-based thermoplastic elastomer is contained is preferably 1 to 30 wt %, with 5 to 30 wt % being even better.

Specific examples include a polymer alloy composed of a styrene-based thermoplastic elastomer, a polyester resin, and a polyester-based thermoplastic elastomer; a polymer alloy composed of a styrene-based thermoplastic elastomer, a polyester resin, and a polyamide resin or polyamide-based thermoplastic elastomer; a polymer alloy composed of a styrene-based thermoplastic elastomer, a polyester resin, and a polyurethane; a polymer alloy composed of a styrene-based thermoplastic elastomer, a polyester-based thermoplastic elastomer, and a polyamide resin or polyamide-based thermoplastic elastomer; a polymer alloy composed of a styrene-based thermoplastic elastomer, a polyester-based thermoplastic elastomer, and a polyurethane; a polymer alloy composed of a styrene-based thermoplastic elastomer, a polyamide resin, and a polyamide-based thermoplastic elastomer; a polymer alloy composed of a styrene-based thermoplastic elastomer, a polyamide resin or polyamide-based thermoplastic elastomer, and a polyurethane; and a polymer alloy composed of a styrene-based thermoplastic elastomer, a polyamide resin or polyamide-based thermoplastic elastomer, and a polyphenylene ether.

The bursting strength of the balloon decreases as the proportions of styrene-based thermoplastic elastomer and polyolefin increase, and the wrapping characteristics and wrapping shape retention of the balloon improve as the proportion of polyolefin increases, but there is a tendency for the balloon walls to become thicker, so the alloy proportions are selected according to the desired characteristics. An example of a favorable combination is a polymer alloy containing 5 to 30 wt % styrene-based thermoplastic elastomer, 50 to 80 wt % polyethylene terephthalate, and 5 to 40 wt % polyolefin (where the total of the three is 100 wt %).

Because the styrene-based thermoplastic elastomer lends itself so well to resin modification, and is also miscible in other materials, it can serve as a general miscibilizer to miscibilize materials that used to be immiscible, facilitating the combination of two or more resins having favorable properties for use as a balloon.

This balloon is manufactured by placing in a mold a tubular parison of the appropriate material, diameter, and wall thickness for forming a balloon, and then blow molding this parison. The balloon is made by blow stretching so that it will be strong enough to withstand the pressure to which it is subjected during inflation, but it is preferable for the tube to be pre-stretched in the axial direction prior to blow molding. After this axial stretching, it is favorable to apply a high internal pressure to the tubular parison at a relatively low temperature, and to pre-inflate and deform the balloon radially to a diameter smaller than the final balloon outside diameter. The tube is blown after its axial stretching, which stretches the tube in the radial direction and forms a balloon. After this blowing, a heat fixing treatment is performed as needed in order to fix the shape and dimensions of the balloon or to increase its strength.

The balloon pertaining to the present invention will now be described in further detail through the following working examples.

Working Example 16

As a polymer alloy material having a styrene-based thermoplastic elastomer as one of its constituent components, mixed pellets composed of 5 wt % styrene-based thermoplastic elastomer ("M1913," made by Asahi Chemical) that was a functional group-endowed hydrogenated styrene-butadiene-styrene block copolymer type (f-SEBS) and that had a specific gravity of 0.92 and an MFR (melt flow rate) of 2.0 g/10 min, and 95 wt % PET with a specific gravity of 1.34 and an intrinsic viscosity of 1.17, were mixed and extruded in a twin-screw extruder to produce polymer alloy pellets. These were molded in a tube-molding extruder into a tubular parison with an outside diameter of 0.78 mm and an inside diameter of 0.36 mm. Next, the parison was put into a metal mold having a straight pipe section with an inside diameter of 1.5 mm, and a preform was molded by applying a pressure of 4.6 MPa inside the tube while applying stress of approximately 0.05 MPa in the axial direction at a mold temperature of 75° C. This preform was taken out of the mold and then repositioned in a mold with a straight pipe inside diameter of 2.5 mm, a pressure of 2.1 MPa was applied at a mold temperature of 105° C., and the mold temperature was then raised to 120° C. while the pressure was raised to 3.6 MPa at the same time. This state was maintained for 60 seconds, after which the mold was cooled and the pressure released, and the balloon was taken out.

Working Example 17

A balloon was manufactured in the same manner as in Working Example 16 except that mixed pellets composed of 10 wt % styrene-based thermoplastic elastomer ("M1913," made by Asahi Chemical) that was a functional group-endowed hydrogenated styrene-butadiene-styrene block copolymer type (f-SEBS) and that had a specific gravity of 0.92 and an MFR (melt flow rate) of 2.0 g/10 min, and 90 wt % PET with a specific gravity of 1.34 and an intrinsic viscosity of 1.17, was used as the polymer alloy material having a styrene-based thermoplastic elastomer as one of its constituent components.

Working Example 18

As a polymer alloy material having a styrene-based thermoplastic elastomer as one of its constituent components, mixed pellets composed of 15 wt % styrene-based thermoplastic elastomer ("M1913," made by Asahi Chemical) that was a functional group-endowed hydrogenated styrene-butadiene-styrene block copolymer type (f-SEBS) and that had a specific gravity of 0.92 and an MFR (melt flow rate) of 2.0 g/10 min, and 85 wt % PET with a specific gravity of 1.34 and an intrinsic viscosity of 1.17, were mixed and extruded in a twin-screw extruder to produce polymer alloy pellets. These were molded in a tube-molding extruder into a tubular parison with an outside diameter of 0.78 mm and an inside diameter of 0.36 mm. Next, the parison was put into a metal mold having a straight pipe section with an inside diameter of 1.5 mm, and a preform was molded by applying a pressure of 3.1 MPa inside the tube while applying stress of approximately 0.04 MPa in the axial direction at a mold temperature of 70° C. This preform was taken out of the mold and then repositioned in a mold with a straight pipe inside diameter of 2.5 mm, a pressure of 2.1 MPa was applied at a mold temperature of 105° C., and the mold temperature was then raised to 120° C. while the pressure was raised to 3.6 MPa at the same time. This state was maintained for 60 seconds, after which the mold was cooled and the pressure released, and the balloon was taken out.

thalate (PET) balloon (Comparative Example 10), a commercially available polyamide (PA) balloon (Comparative Example 11), and a commercially available polyurethane thermoplastic elastomer (PU-based TPE) balloon (Comparative Example 12) were compared by applying pressure until the balloons burst in a 37° C. environment. These results are given in Table 6 below. The calculated strength (δ) of the balloons was determined from the following equation for internal pressure applied to the balloon.

$$\delta = PD/2T$$

P: internal pressure (kfg/cm$^2$) applied to the balloon
D: initial balloon diameter (diameter (mm) at 2 kfg/cm$^2$)
T: balloon wall thickness (mm)
Compliance is defined as the increase in balloon diameter per unit of pressure (kfg/cm$^2$)

TABLE 6

| Type of sample | Constituent materials | Wall thickness (mm) | Bursting pressure (kfg/cm$^2$) | Calculated strength (kfg/cm$^2$) | Compliance (mm/(kfg/cm$^2$)) |
|---|---|---|---|---|---|
| W. E. 16 | f-SEBS/PET = 5/95 | 17 | 24 (2.35 MPa) | 1694 (166 MPa) | 0.014 (0.143 mm/MPa) |
| W. E. 17 | f-SEBS/PET = 10/90 | 19 | 22 (2.16 MPa) | 1389 (136 MPa) | 0.022 (0.224 mm/MPa) |
| W. E. 18 | f-SEBS/PET = 15/85 | 23 | 19 (1.86 MPa) | 991 (97 MPa) | 0.035 (0.357 mm/MPa) |
| W. E. 19 | f-SEBS/PET/PE = 5/70/25 | 25 | 22 (1.96 MPa) | 1064 (104 MPa) | 0.023 (0.235 mm/MPa) |
| C. E. 9 | PE | 30 | 17 (1.67 MPa) | 667 (65 MPa) | 0.033 (0.337 mm/MPa) |
| C. E. 10 | PET | 11 | 22 (2.16 MPa) | 2470 (242 MPa) | 0.009 (0.092 mm/MPa) |
| C. E. 11 | PA | 11 | 21 (2.06 MPa) | 2262 (222 MPa) | 0.025 (0.255 mm/MPa) |
| C. E. 12 | PU-based TPE | 24 | 23 (2.25 MPa) | 987 (97 MPa) | 0.011 (0.112 mm/MPa) |

[W. E.: Working Example, C. E.: Comparative Example]

Working Example 19

As a polymer alloy material having a styrene-based thermoplastic elastomer as one of its constituent components, mixed pellets composed of 5 wt % styrene-based thermoplastic elastomer ("M1913," made by Asahi Chemical) that was a functional group-endowed hydrogenated styrene-butadiene-styrene block copolymer type (f-SEBS) and that had a specific gravity of 0.92 and an MFR (melt flow rate) of 2.0 g/10 min, 70 wt % PET with a specific gravity of 1.34 and an intrinsic viscosity of 1.17, and 25 wt % polyethylene with a density of 0.96, an MFR of 0.7, and an Olsen rigidity of 10,000 were mixed and extruded in a twin-screw extruder to produce polymer alloy pellets. These were molded in a tube-molding extruder into a tubular parison with an outside diameter of 0.78 mm and an inside diameter of 0.36 mm. Next, the parison was put into a metal mold having a straight pipe section with an inside diameter of 2.5 mm, and a balloon was molded by applying a pressure of 0.9 MPa into the tube while applying stress of approximately 0.02 MPa in the axial direction at a mold temperature of 120° C.

The balloons of the above Working Examples 16 to 19, a commercially available polyethylene balloon (Comparative Example 9), a commercially available polyethylene tereph- The results in Table 6 reveal that the balloons of Working Examples 16 to 19 of the present invention were such that compliance could be controlled over a wide range, from 0.014 to 0.035, and had sufficient bursting strength. With the commercially available PET balloon of Comparative Example 10, the balloon itself was hard, it did not conform well to the blood vessel when inflated, and it did not wrap well, so the balloon formed wings along the main part of the catheter when wrapped, and the creased areas were susceptible to pinhole bursting. On the other hand, these problems were not encountered with the balloons of Working Examples 16 to 19 because they all had both pressure resistance and flexibility.

Also, whereas the balloons of Working Examples 16 to 19 of the present invention exhibited relatively good wrapping, rewrapping after inflation, and wrapping shape retention, the PET balloon of Comparative Example 10, the PA balloon of Comparative Example 11, and the PU-based TPE balloon of Comparative Example 12 had poor wrapping shape retention and rewrapping after inflation. In particular, the balloon of Working Example 19 had excellent wrapping shape retention even after a high pressure had been applied, and whereas the wrapping shape was lost after pressurization over 1 MPa with the PE balloon of Comparative Example 9, which had relatively superior wrapping shape retention, the balloon of Working Example 19 retained its wrapping shape.

Furthermore, the balloons of Working Examples 16 to 19 were also improved in terms of friction when wet. Also, the PU-based TPE balloon of Comparative Example 12 was seen to shrink by approximately 18% from its nominal diameter, the cause of which is believed to be heat shrinkage during sterilization and wrapping heat fixing, but the balloons of Working Examples 16 to 19 shrank by only 2 to 3% after sterilization, exhibiting excellent stability.

As seen above, the balloon pertaining to the present invention has excellent flexibility and pressure resistance, and has good wrapping, rewrapping after inflation, and wrapping shape retention. Also, the balloon pertaining to the present invention has excellent adhesion and miscibility with other materials, which is advantageous in terms of assembly, and also makes the balloon safer to use. This material also has excellent coatability, so the various coatings required for a balloon catheter can be applied freely, and the holding capacity thereof is also excellent.

INDUSTRIAL APPLICABILITY

As discussed above, the balloon catheter pertaining to the present invention and the method for manufacturing the same are suited to use in the fields of in percutaneous transluminal angioplasty (PTA) or percutaneous transluminal coronary angioplasty (PTCA), in which constricted areas or obstructions such as in the coronary artery, limb arteries, the renal artery, or peripheral vessels are treated by dilation.

What is claimed is:

1. A balloon catheter having:
   a catheter shaft with a double-tube structure comprising an outer tube and an inner tube through which a guide wire is passed, located at least in proximity of a distal end portion of the catheter, an inflation lumen through which a pressure fluid is passed being provided between said inner tube and said outer tube; and
   a balloon disposed at the distal end portion of said catheter shaft and capable of being inflated, deflated, and wrapped by said pressure fluid,
   wherein an end of said balloon on a proximal side is joined in proximity to the distal end portion of said outer tube, while the other end of said balloon on the distal side is joined in proximity to the distal end portion of said inner tube, and
   a guide tube having an outside diameter smaller than the inside diameter of said outer tube and having an inside diameter larger than the outside diameter of said inner tube is disposed at least at the distal end portion of said outer tube being fixedly attached thereto so as to form a double-tube with said outer tube, and said inner tube is not fixed, but movably extends concentrically through the interior of said guide tube in the axial direction.

2. The balloon catheter defined in claim 1, wherein said guide tube is joined in a state of being offset to an inner wall surface of the outer tube.

3. The balloon catheter defined in claim 1 or 2, where an end tip of said guide tube butts up against the proximal end side of an x-ray impermeable marker joined to the inner tube.

4. The balloon catheter defined in claim 1 or 2, wherein an end tip of said guide tube butts up against the joint where the balloon joins to the inner tube.

5. The balloon catheter defined in claim 1, wherein wall thickness of said guide tube decreases toward the end tip.

6. The balloon catheter defined in claim 1, wherein an X-ray impermeable marker is provided over the outer surface of said guide tube.

7. The balloon catheter defined in claim 1, wherein said guide tube is composed of a polyimide.

8. The balloon catheter defined in claim 1, wherein said guide tube is at least composed of one or more members of the group consisting of polyamide elastomers, polyester elastomers, polyurethane elastomers, and polyolefin elastomers.

9. The balloon catheter defined in claim 1, wherein a spring-like coil is embedded in said guide tube.

10. The balloon catheter defined in claim 9, wherein said spring-like coil is composed of an X-ray impermeable material.

11. The balloon catheter defined in claim 1, wherein said inner tube protrudes from the balloon distal end portion, and a distal end tip of said inner tube formed at the junction with said distal end portion has a pointed taper shape, and the distal end taper portion has a wall thickness that decreases continuously in said distal end tip from the proximity of the most distal end of the distal end-side balloon joint up to the most distal end of the catheter, the average thickness reduction gradient is 6 to 60 $\mu$m/mm, the length from said most distal end of the distal end-side balloon joint to the most distal end of the catheter is 3 to 10 mm, and the tube wall thickness at the most distal end of said distal end taper portion is 10 to 50 $\mu$m.

12. The balloon catheter defined in claim 11, wherein said average thickness reduction gradient of the distal end taper portion is 10 to 30 $\mu$m/mm, the length from said most distal end of the distal end-side balloon joint to the most distal end of the catheter is 4 to 7 mm, and the tube wall thickness at the most distal end of said distal end taper portion is 20 to 40 $\mu$m.

13. The balloon catheter defined in claim 11 or 12, wherein an adhesive agent layer is formed at a portion containing a step produced between said inner tube and the most distal end of said distal end-side balloon joint so as to eliminate said step, decreasing the discontinuity in rigidity and the step in the proximity of the balloon catheter distal end portion.

14. The balloon catheter defined in claim 11 or 12, wherein the most distal end of a sleeve portion of the distal end-side balloon joint is formed in a taper decreasing the discontinuity in rigidity and a step in the proximity of the balloon catheter distal end portion.

15. The balloon catheter defined in claim 11, wherein the most distal end of said distal end taper portion is chamfered.

16. The balloon catheter defined in claim 11, wherein said inner tube is composed of HDPE (High-Density PolyEthylene) or a fluororesin such as polytetrafluoroethylene.

17. The balloon catheter defined in claim 1, wherein a durometer hardness (D value) indicating the state of curing of an adhesive agent used to join the proximal end of said balloon in the proximity of the distal end portion of said outer tube and to join the distal end of said balloon in the proximity of the distal end portion of said inner tube is at least D16 and no more the D70.

18. The balloon catheter defined in claim 17, wherein said durometer hardness (D value) of the adhesive agent is at least D30 and no more than D70.

19. The balloon catheter defined in claim 17, wherein said adhesive agent is a two-liquid normal temperature (room temperature) curing type of adhesive agent.

20. The balloon catheter defined in claim 19, wherein said two-liquid normal temperature (room temperature) curing type of adhesive agent is a urethane-based adhesive agent.

21. The balloon catheter defined in claim 19, wherein said two-liquid normal temperature (room temperature) curing type of adhesive agent is a silicone-based adhesive agent.

22. The balloon catheter defined in claim 19, wherein said two-liquid normal temperature (room temperature) curing type of adhesive agent is an epoxy-based adhesive agent.

23. The balloon catheter defined in claim 17, wherein said adhesive agent is a UV-curing adhesive agent.

24. The balloon catheter defined in claim 17, wherein said adhesive agent is a water-absorption curing type of adhesive agent.

25. The balloon catheter defined in claim 24, wherein said water-absorption curing type of adhesive agent is a cyanoacrylate-based adhesive agent.

26. The balloon catheter defined in claim 24, wherein said water-absorption curing type of adhesive agent is a urethane-based adhesive agent.

27. The balloon catheter defined in claim 1, wherein said balloon is composed of a polymer alloy material including a styrene-based thermoplastic elastomer as a constituent component.

28. The balloon defined in claim 27, wherein said polymer alloy material includes one or more members of the group consisting of polyester resins, polyester-based thermoplastic elastomers, polyamide resins, polyamide-based thermoplastic elastomers, polyurethanes, and polyphenylene ethers as constituent components.

29. The balloon defined in claim 27 or 28, wherein said polymer alloy material includes a polyolefin as a constituent component.

30. The balloon defined in claim 27, wherein said styrene-based thermoplastic elastomer is contained in an amount of 1 to 30 wt %.

31. The balloon defined in claim 27, wherein said styrene-based thermoplastic elastomer is a type that imparts functional groups.

32. The balloon defined in claim 27, wherein said styrene-based thermoplastic elastomer is a hydrogenation type.

* * * * *